United States Patent [19]

Kari

[11] Patent Number: 5,654,274
[45] Date of Patent: Aug. 5, 1997

[54] BIOLOGICALLY ACTIVE PEPTIDES HAVING N-TERMINAL SUBSTITUTIONS

[75] Inventor: U. Prasad Kari, Lansdale, Pa.

[73] Assignee: Magainin Pharmaceuticals, Inc., Plymouth Meeting, Pa.

[21] Appl. No.: 404,283

[22] Filed: Mar. 14, 1995

Related U.S. Application Data

[63] Continuation of Ser. No. 184,462, Jan. 18, 1994, abandoned, which is a continuation-in-part of Ser. No. 891,201, Jun. 1, 1992, abandoned.

[51] Int. Cl.$^6$ .................... A61K 38/00; C07K 14/00
[52] U.S. Cl. ............................. 514/12; 530/324
[58] Field of Search ................. 530/324; 514/12

[56] References Cited

U.S. PATENT DOCUMENTS

| | | | |
|---|---|---|---|
| 5,070,188 | 12/1991 | Njieha et al. | 530/324 |
| 5,114,921 | 5/1992 | Zasloff | 514/12 |
| 5,221,664 | 6/1993 | Berkowitz et al. | 514/12 |
| 5,294,605 | 3/1994 | Houghten et al. | 514/13 |
| 5,358,934 | 10/1994 | Borovsky et al. | 514/17 |
| 5,424,290 | 6/1995 | Maloy et al. | 514/12 |
| 5,470,950 | 11/1995 | Maloy et al. | 530/324 |

FOREIGN PATENT DOCUMENTS

| | | |
|---|---|---|
| 8911290 | 11/1990 | WIPO . |
| 9112015 | 8/1991 | WIPO . |
| 9116066 | 10/1991 | WIPO . |
| 9117760 | 11/1991 | WIPO . |
| 9200090 | 1/1992 | WIPO . |

OTHER PUBLICATIONS

Peter Hunter, *Gen. Microbiology*—The Student's—Textbook, Mosby Company, pp. 19, 34–46, 1977.

Prasad et al., SAR studies on PGLa: An antimicrobial peptide isolated from frog skin extracts, Peptides 1992, Proceedings of the 22nd Euopean Peptide Symposium, pp. 755–756.

Kato et al., "Conformational Studies of Amphipathic α-helical Peptides Containing an Amino Acid with a Long Alkyl Chain and their Anchoring to Lipid Bilayer Liposomes," Biochimica et Biophysica Acta, 1063–191–196 (1991).

A1–Obeidi et al., "Synthesis and Biological Activities of Fatty Acid Conjugates of a Cyclic Lactam α–Melanotropin," J. Med. Chem., 35:118–123 (1992).

Christensen et al., "Channel–forming Properties of Cecropins and Related Model Compounds Incorporated into Planar Liquid Membranes," PNAS, 85:5072–5076 (1988).

Richter et al., "Sequence of Preparocaerulein cDNAs As Cloned from Skin of Xenopus Laevis," J. Biol. Chem., 261(8): 3676–3680 (1986).

Gibson et al., "Novel Peptide Fragments Originating from PGL$^a$ and the Caeurulein and Xenopsin Precursors from *Xenopus laevis*," J. Biol. Chem., 261(12):5341–5349 (1986).

Wakabayashi et al., "Complete Nucleotide Sequence of mRNA for Caerulein Precursor from Xenopus Skin: the mRNA Contains an Unusual Repetitive Structure," Nucleic Acids Research 13(6):1817–1828 (1985).

*Primary Examiner*—Cecilia J. Tsang
*Assistant Examiner*—S. G. Marshall
*Attorney, Agent, or Firm*—Finnegan, Henderson, Farabow, Garrett & Dunner, L.L.P.

[57] ABSTRACT

An N-terminal substituted peptide or protein having the formula:

$$\begin{array}{c} W \\ | \\ T-N-X. \end{array}$$

X is a biologically active amphiphilic ion channel-forming peptide or protein. T is a lipophilic moiety, and preferably, T is:

$$\begin{array}{c} O \\ \| \\ R-C-, \end{array}$$

wherein R is a hydrocarbon (alkyl or aromatic or alkylaromatic) having at least 2 and no more than 10 carbon atoms. T is preferably an octanoyl group. W is T or hydrogen. The N-terminal substituted peptides and proteins have improved biological activity against target cells, viruses, and vitally-infected cells.

69 Claims, No Drawings

SEQUENCE LISTING ( 1 ) GENERAL INFORMATION:

( i i i ) NUMBER OF SEQUENCES: 153

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ala  Phe  Ser  Lys  Ala  Phe  Ser  Lys  Ala  Phe  Ser  Lys  Ala  Phe  Ser  Lys
1                  5                      10                      15
Ala  Phe  Ser  Lys
               20
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Ala  Phe  Ser  Lys  Ala  Phe  Ser  Lys  Ala  Phe  Ser  Lys  Ala  Phe  Ser  Lys
1                  5                      10                      15
Ala  Phe  Ser  Lys  Ala  Phe  Ser  Lys
               20
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Phe  Ser  Lys  Ala  Phe  Ser  Lys  Ala  Phe  Ser  Lys  Ala  Phe  Ser  Lys  Ala
1                  5                      10                      15
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Ser  Lys  Ala  Phe  Ser  Lys  Ala  Phe  Ser  Lys  Ala  Phe  Ser  Lys  Ala  Phe
1                  5                      10                      15
```

```
            Ser  Lys  Ala  Phe
                      20
```

( 2 ) INFORMATION FOR SEQ ID NO:5:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

```
Lys  Ala  Phe  Ser  Lys  Ala  Phe  Ser  Lys  Ala  Phe  Ser  Lys  Ala  Phe  Ser
 1                  5                        10                       15
```

( 2 ) INFORMATION FOR SEQ ID NO:6:

( i ) SEQUENCE CHARACTERISTICS:
    ( A ) LENGTH: 23 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

```
Gly  Ile  Gly  Lys  Phe  Leu  His  Ser  Ala  Gly  Lys  Phe  Gly  Lys  Ala  Phe
 1                  5                        10                       15

Val  Gly  Glu  Ile  Met  Lys  Ser
                20
```

( 2 ) INFORMATION FOR SEQ ID NO:7:

( i ) SEQUENCE CHARACTERISTICS:
    ( A ) LENGTH: 23 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:7:

```
Gly  Ile  Gly  Lys  Phe  Leu  His  Ser  Ala  Lys  Lys  Phe  Gly  Lys  Ala  Phe
 1                  5                        10                       15

Val  Gly  Glu  Ile  Met  Asn  Ser
                20
```

( 2 ) INFORMATION FOR SEQ ID NO:8:

( i ) SEQUENCE CHARACTERISTICS:
    ( A ) LENGTH: 22 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:8:

```
Gly  Ile  Gly  Lys  Phe  Leu  His  Ser  Ala  Lys  Lys  Phe  Gly  Lys  Ala  Phe
 1                  5                        10                       15

Val  Gly  Glu  Ile  Met  Asn
                20
```

( 2 ) INFORMATION FOR SEQ ID NO:9:

( i ) SEQUENCE CHARACTERISTICS:
    ( A ) LENGTH: 22 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:9:

```
Ile Gly Lys Phe Leu His Ser Ala Lys Lys Phe Gly Lys Ala Phe Val
1               5                   10                  15

Gly Glu Ile Met Asn Ser
            20
```

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Gly Lys Phe Leu His Ser Ala Lys Lys Phe Gly Lys Ala Phe Val Gly
1               5                   10                  15

Glu Ile Met Asn Ser
            20
```

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Lys Phe Leu His Ser Ala Lys Lys Phe Gly Lys Ala Phe Val Gly Glu
1               5                   10                  15

Ile Met Asn Ser
        20
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Gly Met Ala Ser Lys Ala Gly Ala Ile Ala Gly Lys Ile Ala Lys Val
1               5                   10                  15

Ala Leu Lys Ala Leu
            20
```

( 2 ) INFORMATION FOR SEQ ID NO:13:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Gly Trp Ala Ser Lys Ile Gly Gln Thr Leu Gly Lys Ile Ala Lys Val
1               5                   10                  15

Gly Leu Lys Glu Leu Ile Gln Pro Lys
```

20                    25

(2) INFORMATION FOR SEQ ID NO:14:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:14:

```
Gly Phe Gly Ser Phe Leu Gly Leu Ala Leu Lys Ala Ala Leu Lys Ile
1               5                   10                  15
Gly Ala Asn Ala Leu Gly Gly Ala Pro Gln Gln
                20                  25
```

(2) INFORMATION FOR SEQ ID NO:15:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:15:

```
Gly Leu Ala Ser Phe Leu Gly Lys Ala Leu Lys Ala Gly Leu Lys Ile
1               5                   10                  15
Gly Ala His Leu Leu Gly Gly Ala Pro Gln Gln
                20                  25
```

(2) INFORMATION FOR SEQ ID NO:16:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:16:

```
Gly Leu Ala Ser Leu Leu Gly Lys Ala Leu Lys Ala Gly Leu Lys Ile
1               5                   10                  15
Gly Thr His Phe Leu Gly Gly Ala Pro Gln Gln
                20                  25
```

(2) INFORMATION FOR SEQ ID NO:17:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:17:

```
Gly Leu Ala Ser Leu Leu Gly Lys Ala Leu Lys Ala Thr Leu Lys Ile
1               5                   10                  15
Gly Thr His Phe Leu Gly Gly Ala Pro Gln Gln
                20                  25
```

(2) INFORMATION FOR SEQ ID NO:18:

(i) SEQUENCE CHARACTERISTICS:
        (A) LENGTH: 27 amino acids
        (B) TYPE: amino acid (D) TOPOLOGY: linear (ii) MOLECULE TYPE: peptide (xi) SEQUENCE DESCRIPTION: SEQ ID NO:18:

Gly Phe Ala Ser Phe Leu Gly Lys Ala Leu Lys Ala Ala Leu Lys Ile
1               5                   10                  15

Gly Ala Asn Met Leu Gly Gly Thr Pro Gln Gln
                20                  25

(2) INFORMATION FOR SEQ ID NO:19:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (xi) SEQUENCE DESCRIPTION: SEQ ID NO:19:

Gly Phe Gly Ser Phe Leu Gly Lys Ala Leu Lys Ala Ala Leu Lys Ile
1               5                   10                  15

Gly Ala Asn Ala Leu Gly Gly Ala Pro Gln Gln
                20                  25

(2) INFORMATION FOR SEQ ID NO:20:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (xi) SEQUENCE DESCRIPTION: SEQ ID NO:20:

Gly Phe Gly Ser Phe Leu Gly Lys Ala Leu Lys Ala Ala Leu Lys Ile
1               5                   10                  15

Gly Ala Asn Ala Leu Gly Gly Ser Pro Gln Gln
                20                  25

(2) INFORMATION FOR SEQ ID NO:21:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (xi) SEQUENCE DESCRIPTION: SEQ ID NO:21:

Gly Phe Ala Ser Phe Leu Gly Lys Ala Leu Lys Ala Ala Leu Lys Ile
1               5                   10                  15

Gly Ala Asn Leu Leu Gly Gly Thr Pro Gln Gln
                20                  25

(2) INFORMATION FOR SEQ ID NO:22:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (xi) SEQUENCE DESCRIPTION: SEQ ID NO:22:

Gly Phe Ala Ser Phe Leu Gly Lys Ala Leu Lys Ala Ala Leu Lys Ile
1               5                   10                  15

```
         Gly  Ala  Asn  Ala  Leu  Gly  Gly  Ala  Pro  Gln  Gln
                        20                       25
```

( 2 ) INFORMATION FOR SEQ ID NO:23:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
         Gly  Phe  Ala  Ser  Phe  Leu  Gly  Lys  Ala  Leu  Lys  Ala  Ala  Leu  Lys  Ile
         1                   5                        10                           15

Gly  Ala  Asn  Met  Leu  Gly  Gly  Ala  Pro  Gln  Gln
                        20                       25
```

( 2 ) INFORMATION FOR SEQ ID NO:24:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
         Gly  Phe  Gly  Ser  Phe  Leu  Gly  Lys  Ala  Leu  Lys  Ala  Ala  Leu  Lys  Ile
         1                   5                        10                           15

Gly  Ala  Asn  Ala  Leu  Gly  Gly  Ser  Leu  Gln  Gln
                        20                       25
```

( 2 ) INFORMATION FOR SEQ ID NO:25:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
         Gly  Phe  Gly  Ser  Phe  Leu  Gly  Lys  Ala  Leu  Lys  Ala  Gly  Leu  Lys  Ile
         1                   5                        10                           15

Gly  Thr  Asn  Phe  Leu  Gly  Gly  Ala  Pro  Gln  Gln
                        20                       25
```

( 2 ) INFORMATION FOR SEQ ID NO:26:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
         Gly  Leu  Ala  Ser  Leu  Leu  Gly  Lys  Ala  Leu  Lys  Ala  Ala  Leu  Lys  Ile
         1                   5                        10                           15

Gly  Ala  Asn  Ala  Leu  Gly  Gly  Ser  Pro  Gln  Gln
                        20                       25
```

( 2 ) INFORMATION FOR SEQ ID NO:27:

( i ) SEQUENCE CHARACTERISTICS:

( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:27:

```
Lys Ile Ala Gly Lys Ile Ala Lys Ile Ala Gly Lys Ile Ala Lys Ile
1               5                   10                  15
Ala Gly Lys Ile Ala
            20
```

( 2 ) INFORMATION FOR SEQ ID NO:28:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:28:

```
Lys Ile Ala Lys Ile Ala Gly Lys Ile Ala Lys Ile Ala Gly Lys Ile
1               5                   10                  15
Ala Lys Ile Ala Gly
            20
```

( 2 ) INFORMATION FOR SEQ ID NO:29:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:29:

```
Lys Ile Ala Gly Lys Ile Gly Lys Ile Ala Gly Lys Ile Gly Lys Ile
1               5                   10                  15
Ala Gly Lys Ile Gly
            20
```

( 2 ) INFORMATION FOR SEQ ID NO:30:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:30:

```
Lys Leu Ala Gly Lys Leu Ala Lys Leu Ala Gly Lys Leu Ala Lys Leu
1               5                   10                  15
Ala Gly Lys Leu Ala
            20
```

( 2 ) INFORMATION FOR SEQ ID NO:31:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:31:

```
Lys  Phe  Ala  Gly  Lys  Phe  Ala  Lys  Phe  Ala  Gly  Lys  Phe  Ala  Lys  Phe
 1                    5                         10                        15

Ala  Gly  Lys  Phe  Ala
                2 0
```

( 2 ) INFORMATION FOR SEQ ID NO:32:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

```
Lys  Ala  Leu  Ser  Lys  Ala  Leu  Lys  Ala  Leu  Ser  Lys  Ala  Leu  Lys  Ala
 1                    5                         10                        15

Leu  Ser  Lys  Ala  Leu
                2 0
```

( 2 ) INFORMATION FOR SEQ ID NO:33:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

```
Lys  Leu  Leu  Lys  Ala  Leu  Gly  Lys  Leu  Leu  Lys  Ala  Leu  Gly  Lys  Leu
 1                    5                         10                        15

Leu  Lys  Ala  Leu  Gly
                2 0
```

( 2 ) INFORMATION FOR SEQ ID NO:34:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
Lys  Ala  Ile  Gly  Lys  Ala  Ile  Lys  Ala  Ile  Gly  Lys  Ala  Ile  Lys  Ala
 1                    5                         10                        15

Ile  Gly  Lys  Ala  Ile
                2 0
```

( 2 ) INFORMATION FOR SEQ ID NO:35:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

```
Gly  Ile  Ala  Lys  Ile  Ala  Lys  Gly  Ile  Ala  Lys  Ile  Ala  Lys  Gly  Ile
 1                    5                         10                        15

Ala  Lys  Ile  Ala  Lys
                2 0
```

( 2 ) INFORMATION FOR SEQ ID NO:36:

( i ) SEQUENCE CHARACTERISTICS:
 ( A ) LENGTH: 21 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:36:

Lys Ile Ala Lys Ile Phe Gly Lys Ile Ala Lys Ile Phe Gly Lys Ile
1               5                   10                  15

Ala Lys Ile Phe Gly
            20

( 2 ) INFORMATION FOR SEQ ID NO:37:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:37:

Gly Ile Ala Arg Ile Ala Lys Gly Ile Ala Arg Ile Ala Lys Gly Ile
1               5                   10                  15

Ala Arg Ile Ala Lys
            20

( 2 ) INFORMATION FOR SEQ ID NO:38:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:38:

Lys Phe Ala Arg Ile Ala Gly Lys Phe Ala Arg Ile Ala Gly Lys Phe
1               5                   10                  15

Ala Arg Ile Ala Gly
            20

( 2 ) INFORMATION FOR SEQ ID NO:39:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:39:

Gly Phe Ala Lys Ile Ala Lys Gly Phe Ala Lys Ile Ala Lys Gly Phe
1               5                   10                  15

Ala Lys Ile Ala Lys
            20

( 2 ) INFORMATION FOR SEQ ID NO:40:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: peptide ( i x ) FEATURE:
   ( A ) NAME/KEY: Modified-site
   ( B ) LOCATION: one-of(5, 12, 19)
   ( D ) OTHER INFORMATION: /note="Xaa is ornithine."

( x i ) SEQUENCE DESCRIPTION: SEQ ID NO:40:

```
Lys Ile Ala Gly Xaa Ile Ala Lys Ile Ala Gly Xaa Ile Ala Lys Ile
1               5                   10                  15
Ala Gly Xaa Ile Ala
            20
```

( 2 ) INFORMATION FOR SEQ ID NO:41:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:41:

```
Lys Ile Ala Arg Ile Ala Gly Lys Ile Ala Arg Ile Ala Gly Lys Ile
1               5                   10                  15
Ala Arg Ile Ala Gly
            20
```

( 2 ) INFORMATION FOR SEQ ID NO:42:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: one-of(1, 8, 15)
      ( D ) OTHER INFORMATION: /note="Xaa is ornithine."

( x i ) SEQUENCE DESCRIPTION: SEQ ID NO:42:

```
Xaa Ile Ala Gly Lys Ile Ala Xaa Ile Ala Gly Lys Ile Ala Xaa Ile
1               5                   10                  15
Ala Gly Lys Ile Ala
            20
```

( 2 ) INFORMATION FOR SEQ ID NO:43:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:43:

```
Gly Ile Ala Arg Ile Phe Lys Gly Ile Ala Arg Ile Phe Lys Gly Ile
1               5                   10                  15
Ala Arg Ile Phe Lys
            20
```

( 2 ) INFORMATION FOR SEQ ID NO:44:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( i x ) FEATURE:
    ( A ) NAME/KEY: Modified-site
    ( B ) LOCATION: one-of(2, 6, 9, 13, 16, 20)
    ( D ) OTHER INFORMATION: /note="Xaa is norleucine."

( x i ) SEQUENCE DESCRIPTION: SEQ ID NO:44:

```
Lys  Xaa  Ala  Gly  Lys  Xaa  Ala  Lys  Xaa  Ala  Gly  Lys  Xaa  Ala  Lys  Xaa
1                 5                            10                           15

Ala  Gly  Lys  Xaa  Ala
                20
```

( 2 ) INFORMATION FOR SEQ ID NO:45:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: one-of(2, 9, 16)
        ( D ) OTHER INFORMATION: /note="Xaa is norleucine."

( x i ) SEQUENCE DESCRIPTION: SEQ ID NO:45:

```
Lys  Xaa  Ala  Gly  Lys  Ile  Ala  Lys  Xaa  Ala  Gly  Lys  Ile  Ala  Lys  Xaa
1                 5                            10                           15

Ala  Gly  Lys  Ile  Ala
                20
```

( 2 ) INFORMATION FOR SEQ ID NO:46:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: one-of(6, 13, 20)
        ( D ) OTHER INFORMATION: /note="Xaa is norleucine."

( x i ) SEQUENCE DESCRIPTION: SEQ ID NO:46:

```
Lys  Ile  Ala  Gly  Lys  Xaa  Ala  Lys  Ile  Ala  Gly  Lys  Xaa  Ala  Lys  Ile
1                 5                            10                           15

Ala  Gly  Lys  Xaa  Ala
                20
```

( 2 ) INFORMATION FOR SEQ ID NO:47:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: one-of(2, 6, 9, 13, 16, 20)
        ( D ) OTHER INFORMATION: /note="Xaa is norvaline."

( x i ) SEQUENCE DESCRIPTION: SEQ ID NO:47:

```
Lys  Xaa  Ala  Gly  Lys  Xaa  Ala  Lys  Xaa  Ala  Gly  Lys  Xaa  Ala  Lys  Xaa
1                 5                            10                           15
```

```
Ala Gly Lys Xaa Ala
            20
```

(2) INFORMATION FOR SEQ ID NO:48:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(2, 9, 16, 20)
        (D) OTHER INFORMATION: /note="Xaa is norvaline."

(xi) SEQUENCE DESCRIPTION: SEQ ID NO:48:

```
Lys Xaa Ala Gly Lys Ile Ala Lys Xaa Ala Gly Lys Ile Ala Lys Xaa
 1               5                  10                  15
Ala Gly Lys Xaa Ala
            20
```

(2) INFORMATION FOR SEQ ID NO:49:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:49:

```
Lys Leu Leu Ser Lys Leu Gly Lys Leu Leu Ser Lys Leu Gly Lys Leu
 1               5                  10                  15
Leu Ser Lys Leu Gly
            20
```

(2) INFORMATION FOR SEQ ID NO:50:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:50:

```
Lys Leu Leu Ser Lys Phe Gly Lys Leu Leu Ser Lys Phe Gly Lys Leu
 1               5                  10                  15
Leu Ser Lys Phe Gly
            20
```

(2) INFORMATION FOR SEQ ID NO:51:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(6, 13, 20)
        (D) OTHER INFORMATION: /note="Xaa is norvaline."

(xi) SEQUENCE DESCRIPTION: SEQ ID NO:51:

```
Lys  Ile  Ala  Gly  Lys  Xaa  Ala  Lys  Ile  Ala  Gly  Lys  Xaa  Ala  Lys  Ile
1                 5                         10                        15

Ala  Gly  Lys  Xaa  Ala
              20
```

( 2 ) INFORMATION FOR SEQ ID NO:52:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:52:

```
His  Ile  Ala  Gly  His  Ile  Ala  His  Ile  Ala  Gly  His  Ile  Ala  His  Ile
1                 5                         10                        15

Ala  Gly  His  Ile  Ala
              20
```

( 2 ) INFORMATION FOR SEQ ID NO:53:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:53:

```
Ala  Gly  Lys  Ile  Ala  Lys  Ile  Ala  Gly  Lys  Ile  Ala  Lys  Ile  Ala  Gly
1                 5                         10                        15

Lys  Ile  Ala  Lys  Ile
              20
```

( 2 ) INFORMATION FOR SEQ ID NO:54:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:54:

```
Ile  Ala  Lys  Ile  Ala  Gly  Lys  Ile  Ala  Lys  Ile  Ala  Gly  Lys  Ile  Ala
1                 5                         10                        15

Lys  Ile  Ala  Gly  Lys
              20
```

( 2 ) INFORMATION FOR SEQ ID NO:55:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:55:

```
Lys  Ile  Ala  Gly  Arg  Ile  Ala  Lys  Ile  Ala  Gly  Arg  Ile  Ala  Lys  Ile
1                 5                         10                        15

Ala  Gly  Arg  Ile  Ala
              20
```

( 2 ) INFORMATION FOR SEQ ID NO:56:

( i ) SEQUENCE CHARACTERISTICS:
   ( A ) LENGTH: 21 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:56:

Arg Ile Ala Gly Arg Ile Ala Arg Ile Ala Gly Arg Ile Ala Arg Ile
1               5                   10                  15

Ala Gly Arg Ile Ala
        20

( 2 ) INFORMATION FOR SEQ ID NO:57:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:57:

Lys Val Ala Gly Lys Ile Ala Lys Val Ala Gly Lys Ile Ala Lys Val
1               5                   10                  15

Ala Gly Lys Ile Ala
        20

( 2 ) INFORMATION FOR SEQ ID NO:58:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:58:

Lys Ile Ala Gly Lys Val Ala Lys Ile Ala Gly Lys Val Ala Lys Ile
1               5                   10                  15

Ala Gly Lys Val Ala
        20

( 2 ) INFORMATION FOR SEQ ID NO:59:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:59:

Ala Lys Ile Ala Gly Lys Ile Ala Lys Ile Ala Gly Lys Ile Ala Lys
1               5                   10                  15

Ile Ala Gly Lys Ile
        20

( 2 ) INFORMATION FOR SEQ ID NO:60:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( i x ) FEATURE:
    ( A ) NAME/KEY: Modified-site
    ( B ) LOCATION: one-of(1, 5, 8, 12, 15, 19)
    ( D ) OTHER INFORMATION: /note="Xaa is ornithine."

( x i ) SEQUENCE DESCRIPTION: SEQ ID NO:60:

```
Xaa  Ile  Ala  Gly  Xaa  Ile  Ala  Xaa  Ile  Ala  Gly  Xaa  Ile  Ala  Xaa  Ile
1                 5                        10                       15
Ala  Gly  Xaa  Ile  Ala
          20
```

( 2 ) INFORMATION FOR SEQ ID NO:61:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:61:

```
Lys  Phe  Ala  Gly  Lys  Ile  Ala  Lys  Phe  Ala  Gly  Lys  Ile  Ala  Lys  Phe
1                 5                        10                       15
Ala  Gly  Lys  Ile  Ala
          20
```

( 2 ) INFORMATION FOR SEQ ID NO:62:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:62:

```
Lys  Ile  Ala  Gly  Lys  Phe  Ala  Lys  Ile  Ala  Gly  Lys  Phe  Ala  Lys  Ile
1                 5                        10                       15
Ala  Gly  Lys  Phe  Ala
          20
```

( 2 ) INFORMATION FOR SEQ ID NO:63:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: one-of(2, 9, 16)
        ( D ) OTHER INFORMATION: /note="Xaa is cyclohexylalanine."

( x i ) SEQUENCE DESCRIPTION: SEQ ID NO:63:

```
Lys  Xaa  Ala  Gly  Lys  Ile  Ala  Lys  Xaa  Ala  Gly  Lys  Ile  Ala  Lys  Xaa
1                 5                        10                       15
Ala  Gly  Lys  Ile  Ala
          20
```

( 2 ) INFORMATION FOR SEQ ID NO:64:

( i ) SEQUENCE CHARACTERISTICS:
        ( A ) LENGTH: 21 amino acids
        ( B ) TYPE: amino acid
        ( D ) TOPOLOGY: linear (ii) MOLECULE TYPE: peptide (ix) FEATURE:
    (A) NAME/KEY: Modified-site
    (B) LOCATION: one-of(2, 9, 16)
    (D) OTHER INFORMATION: /note="Xaa is norleucine."

(xi) SEQUENCE DESCRIPTION: SEQ ID NO:64:

```
Lys Xaa Ala Lys Ile Ala Gly Lys Xaa Ala Lys Ile Ala Gly Lys Xaa
1               5                   10                  15
Ala Lys Ile Ala Gly
            20
```

(2) INFORMATION FOR SEQ ID NO:65:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:65:

```
Arg Ile Ala Gly Lys Ile Ala Arg Ile Ala Gly Lys Ile Ala Arg Ile
1               5                   10                  15
Ala Gly Lys Ile Ala
            20
```

(2) INFORMATION FOR SEQ ID NO:66:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(1, 5, 8, 12, 15, 19)
        (D) OTHER INFORMATION: /note="Xaa is homoarginine."

(xi) SEQUENCE DESCRIPTION: SEQ ID NO:66:

```
Xaa Ile Ala Gly Xaa Ile Ala Xaa Ile Ala Gly Xaa Ile Ala Xaa Ile
1               5                   10                  15
Ala Gly Xaa Ile Ala
            20
```

(2) INFORMATION FOR SEQ ID NO:67:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(1, 8, 15)
        (D) OTHER INFORMATION: /note="Xaa is
            p- aminophenylalanine"

(xi) SEQUENCE DESCRIPTION: SEQ ID NO:67:

```
Xaa Ile Ala Gly Lys Ile Ala Xaa Ile Ala Gly Lys Ile Ala Xaa Ile
1               5                   10                  15
Ala Gly Lys Ile Ala
            20
```

(2) INFORMATION FOR SEQ ID NO:68:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: one-of(5, 12, 19)
    (D) OTHER INFORMATION: /note="Xaa is
        p- aminophenylalanine."

(xi) SEQUENCE DESCRIPTION: SEQ ID NO:68:

Lys Ile Ala Gly Xaa Ile Ala Lys Ile Ala Gly Xaa Ile Ala Lys Ile
1               5                   10                  15

Ala Gly Xaa Ile Ala
            20

(2) INFORMATION FOR SEQ ID NO:69:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:69:

Lys Leu Ala Ser Lys Ala Gly Lys Ile Ala Gly Lys Ile Ala Lys Val
1               5                   10                  15

Ala Leu Lys Ala Leu
            20

(2) INFORMATION FOR SEQ ID NO:70:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 12
    (C) OTHER INFORMATION: /note="Xaa is ornithine."

(xi) SEQUENCE DESCRIPTION: SEQ ID NO:70:

Lys Ile Ala Gly Lys Ile Ala Lys Ile Ala Gly Xaa Ile Ala Lys Ile Ala
1               5                   10                  15

Gly Lys Ile Ala
        20

(2) INFORMATION FOR SEQ ID NO:71:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:71:

Lys Ile Ala Gly Lys Ile Ala Lys Ile Ala Gly Arg Ile Ala Lys Ile

```
                1               5                    10                   15
          Ala  Gly  Lys  Ile  Ala
                              20
```

( 2 ) INFORMATION FOR SEQ ID NO:72:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /note="Xaa is norleucine."

( x i ) SEQUENCE DESCRIPTION: SEQ ID NO:72:

```
          Lys  Ile  Ala  Gly  Lys  Ile  Ala  Lys  Ile  Ala  Gly  Xaa  Ile  Ala  Lys  Ile
          1                    5                            10                        15
          Ala  Gly  Lys  Ile  Ala
                              20
```

( 2 ) INFORMATION FOR SEQ ID NO:73:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /note="Xaa is norvaline."

( x i ) SEQUENCE DESCRIPTION: SEQ ID NO:73:

```
          Lys  Ile  Ala  Gly  Lys  Ile  Ala  Lys  Ile  Ala  Gly  Xaa  Ile  Ala  Lys  Ile
          1                    5                            10                        15
          Ala  Gly  Lys  Ile  Ala
                              20
```

( 2 ) INFORMATION FOR SEQ ID NO:74:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /note="Xaa is ornithine."

( x i ) SEQUENCE DESCRIPTION: SEQ ID NO:74:

```
          Lys  Phe  Ala  Gly  Lys  Phe  Ala  Lys  Phe  Ala  Gly  Xaa  Phe  Ala  Lys  Phe
          1                    5                            10                        15
          Ala  Gly  Lys  Phe  Ala
                              20
```

( 2 ) INFORMATION FOR SEQ ID NO:75:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /note="Xaa is ornithine."

( x i ) SEQUENCE DESCRIPTION: SEQ ID NO:75:

Lys Ile Ala Gly Lys Phe Ala Lys Ile Ala Gly Xaa Phe Ala Lys Ile
1               5                   10                  15

Ala Gly Lys Phe Ala
            20

( 2 ) INFORMATION FOR SEQ ID NO:76:

( i ) SEQUENCE CHARACTERISTICS:
            ( A ) LENGTH: 21 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: one-of(6, 13, 20)
            ( D ) OTHER INFORMATION: /note="Xaa is norleucine."

( i x ) FEATURE:
            ( A ) NAME/KEY: Modified-site
            ( B ) LOCATION: 12 .
            ( D ) OTHER INFORMATION: /note="Xaa is ornithine."

( x i ) SEQUENCE DESCRIPTION: SEQ ID NO:76:

Lys Ile Ala Gly Lys Xaa Ala Lys Ile Ala Gly Xaa Xaa Ala Lys Ile
1               5                   10                  15

Ala Gly Lys Xaa Ala
            20

( 2 ) INFORMATION FOR SEQ ID NO:77:

( i ) SEQUENCE CHARACTERISTICS:
            ( A ) LENGTH: 21 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:77:

Lys Met Ala Ser Lys Ala Gly Lys Ile Ala Gly Lys Ile Ala Lys Val
1               5                   10                  15

Ala Leu Lys Ala Leu
            20

( 2 ) INFORMATION FOR SEQ ID NO:78:

( i ) SEQUENCE CHARACTERISTICS:
            ( A ) LENGTH: 21 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:78:

Lys Ile Ala Ser Lys Ala Gly Lys Ile Ala Gly Lys Ile Ala Lys Val
1               5                   10                  15

Ala Leu Lys Ala Leu
        20

( 2 ) INFORMATION FOR SEQ ID NO:79:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 9
        ( D ) OTHER INFORMATION: /note="Xaa is norleucine."

( x i ) SEQUENCE DESCRIPTION: SEQ ID NO:79:

Lys Ile Ala Ser Lys Ala Gly Lys Xaa Ala Gly Lys Ile Ala Lys Val
1               5                   10                  15

Ala Leu Lys Ala Leu
        20

( 2 ) INFORMATION FOR SEQ ID NO:80:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 9
        ( C ) OTHER INFORMATION: /note="Xaa is norleucine."

( x i ) SEQUENCE DESCRIPTION: SEQ ID NO:80:

Lys Leu Ala Ser Lys Ala Gly Lys Xaa Ala Gly Lys Ile Ala Lys Val
1               5                   10                  15

Ala Leu Lys Ala Leu
        20

( 2 ) INFORMATION FOR SEQ ID NO:81:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 9
        ( D ) OTHER INFORMATION: /note="Xaa is norleucine."

( x i ) SEQUENCE DESCRIPTION: SEQ ID NO:81:

Lys Xaa Ala Ser Lys Ala Gly Lys Xaa Ala Gly Lys Ile Ala Lys Val
1               5                   10                  15

Ala Leu Lys Ala Leu
        20

( 2 ) INFORMATION FOR SEQ ID NO:82:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /note="Xaa is
            p- aminophenylalanine."

( x i ) SEQUENCE DESCRIPTION: SEQ ID NO:82:

```
Lys  Ile  Ala  Gly  Lys  Ile  Ala  Lys  Ile  Ala  Gly  Xaa  Ile  Ala  Lys  Ile
  1                 5                           10                          15

Ala  Gly  Lys  Ile  Ala
                20
```

( 2 ) INFORMATION FOR SEQ ID NO:83:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

```
Lys  Ile  Ala  Gly  Ala  Ile  Ala  Lys  Ile  Ala  Gly  Lys  Ile  Ala  Lys  Ile
  1                 5                           10                          15

Ala  Gly  Lys  Ile  Ala
                20
```

( 2 ) INFORMATION FOR SEQ ID NO:84:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:84:

```
Lys  Ile  Ala  Gly  Lys  Ile  Ala  Lys  Ile  Ala  Gly  Ala  Ile  Ala  Lys  Ile
  1                 5                           10                          15

Ala  Gly  Lys  Ile  Ala
                20
```

( 2 ) INFORMATION FOR SEQ ID NO:85:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

```
Lys  Ile  Ala  Gly  Lys  Ile  Ala  Lys  Ile  Ala  Gly  Lys  Ile  Ala  Lys  Ile
  1                 5                           10                          15

Ala  Gly  Ala  Ile  Ala
```

20

(2) INFORMATION FOR SEQ ID NO:86:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:86:

```
Lys Ile Ala Lys Lys Ile Ala Lys Ile Ala Lys Lys Ile Ala Lys Ile
1               5                   10                  15
Ala Lys Lys Ile Ala
            20
```

(2) INFORMATION FOR SEQ ID NO:87:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

```
Lys Phe Ala Lys Lys Phe Ala Lys Phe Ala Lys Lys Phe Ala Lys Phe
1               5                   10                  15
Ala Lys Lys Phe Ala
            20
```

(2) INFORMATION FOR SEQ ID NO:88:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:88:

```
Lys Phe Ala Lys Lys Ile Ala Lys Phe Ala Lys Lys Ile Ala Lys Phe
1               5                   10                  15
Ala Lys Lys Ile Ala
            20
```

(2) INFORMATION FOR SEQ ID NO:89:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:89:

```
Ala Ile Ala Gly Lys Ile Ala Lys Ile Ala Gly Lys Ile Ala Lys Ile
1               5                   10                  15
Ala Gly Lys Ile Ala
            20
```

(2) INFORMATION FOR SEQ ID NO:90:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:90:

```
Lys Ile Ala Gly Lys Ile Ala Ala Ile Ala Gly Lys Ile Ala Lys Ile
 1               5                  10                  15
Ala Gly Lys Ile Ala
            20
```

( 2 ) INFORMATION FOR SEQ ID NO:91:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:91:

```
Lys Ile Ala Gly Lys Ile Ala Lys Ile Ala Gly Lys Ile Ala Ala Ile
 1               5                  10                  15
Ala Gly Lys Ile Ala
            20
```

( 2 ) INFORMATION FOR SEQ ID NO:92:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:92:

```
Gly Met Ala Ser Lys Ala Gly Lys Ile Ala Gly Lys Ile Ala Lys Val
 1               5                  10                  15
Ala Leu Lys Ala Leu
            20
```

( 2 ) INFORMATION FOR SEQ ID NO:93:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:93:

```
Gly Ile Gly Ala Val Leu Lys Val Leu Thr Thr Gly Leu Pro Ala Leu
 1               5                  10                  15
Ile Ser Trp Ile Lys Arg Lys Arg Gln Gln
            20                  25
```

( 2 ) INFORMATION FOR SEQ ID NO:94:

( i ) SEQUENCE CHARACTERISTICS:
        ( A ) LENGTH: 11 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:94:

```
Leu Lys Lys Leu Lys Lys Leu Leu Lys Leu Leu
1               5                   10
```

(2) INFORMATION FOR SEQ ID NO:95:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:95:

```
Leu Leu Lys Lys Leu Lys Lys Leu Leu Lys Leu Leu
1               5                   10
```

(2) INFORMATION FOR SEQ ID NO:96:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:96:

```
Lys Leu Leu Lys Lys Leu Lys Lys Leu Leu Lys Leu Leu
1               5                   10
```

(2) INFORMATION FOR SEQ ID NO:97:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:97:

```
Lys Lys Leu Leu Lys Lys Leu Lys Lys Leu Leu Lys Leu Leu
1               5                   10
```

(2) INFORMATION FOR SEQ ID NO:98:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:98:

```
Lys Lys Leu Leu Lys Lys Leu Lys Lys Leu Leu Lys Lys Leu Arg Arg
1               5                   10                  15
```

(2) INFORMATION FOR SEQ ID NO:99:

(i) SEQUENCE CHARACTERISTICS:
      (A) LENGTH: 16 amino acids
      (B) TYPE: amino acid -continued (C) STRANDEDNESS: single
(D) TOPOLOGY: linear (ii) MOLECULE TYPE: peptide (xi) SEQUENCE DESCRIPTION: SEQ ID NO:99:

Lys Leu Lys Lys Leu Leu Lys Lys Leu Lys Lys Leu Leu Lys Leu Leu
1               5                   10                  15

(2) INFORMATION FOR SEQ ID NO:100:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:100:

Leu Lys Lys Leu Leu Lys Lys Leu Lys Lys Leu Leu Lys Lys Asn
1               5                   10                  15

(2) INFORMATION FOR SEQ ID NO:101:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 15
    (D) OTHER INFORMATION: /note="Xaa is homoserine."

(xi) SEQUENCE DESCRIPTION: SEQ ID NO:101:

Leu Lys Lys Leu Leu Lys Lys Leu Lys Lys Leu Leu Lys Lys Xaa
1               5                   10                  15

(2) INFORMATION FOR SEQ ID NO:102:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:102:

Leu Lys Leu Leu Lys Lys Leu Leu Lys Lys Asn Lys Lys Leu Leu Lys
1               5                   10                  15

Lys Leu (2) INFORMATION FOR SEQ ID NO:103:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:103:

Leu Lys Leu Leu Lys Lys Leu Leu Lys Lys Pro Lys Lys Leu Leu Lys
1               5                   10                  15

Lys Leu (2) INFORMATION FOR SEQ ID NO:104:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

```
Leu Leu Lys Lys Leu Lys Lys Leu Leu Lys Lys Leu Gln Gly Pro Pro
1               5                   10                  15
Gln Gly Gln Ser Pro Gln
                20
```

(2) INFORMATION FOR SEQ ID NO:105:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

```
Leu Ala Ser Lys Ala Gly Ala Ile Ala Gly Lys Ile Ala Lys Lys Leu
1               5                   10                  15
Leu Lys Lys Leu
                20
```

(2) INFORMATION FOR SEQ ID NO:106:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

```
Leu Lys Lys Leu Lys Lys Leu
1               5
```

(2) INFORMATION FOR SEQ ID NO:107:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

```
Leu Leu Lys Lys Leu Lys Lys Leu
1               5
```

(2) INFORMATION FOR SEQ ID NO:108:

(i) SEQUENCE CHARACTERISTICS:
        (A) LENGTH: 9 amino acids
        (B) TYPE: amino acid
        (C) STRANDEDNESS: single ( D ) TOPOLOGY: linear ( i i ) MOLECULE TYPE: peptide ( x i ) SEQUENCE DESCRIPTION: SEQ ID NO:108:

Lys Leu Leu Lys Lys Leu Lys Lys Leu
1               5

( 2 ) INFORMATION FOR SEQ ID NO:109:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:109:

Lys Lys Leu Leu Lys Lys Leu Lys Lys Leu
1               5                   10

( 2 ) INFORMATION FOR SEQ ID NO:110:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:110:

Leu Lys Lys Leu Leu Lys Lys Leu Lys Lys Leu
1               5                   10

( 2 ) INFORMATION FOR SEQ ID NO:111:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:111:

Ala Lys Lys Leu Leu Lys Lys Leu Lys Lys Leu
1               5                   10

( 2 ) INFORMATION FOR SEQ ID NO:112:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:112:

Leu Lys Lys Leu Lys Lys Leu Leu Lys Lys Leu
1               5                   10

( 2 ) INFORMATION FOR SEQ ID NO:113:

( i ) SEQUENCE CHARACTERISTICS:
            ( A ) LENGTH: 12 amino acids
            ( B ) TYPE: amino acid
            ( C ) STRANDEDNESS: single ( D ) TOPOLOGY: linear ( i i ) MOLECULE TYPE: peptide ( x i ) SEQUENCE DESCRIPTION: SEQ ID NO:113:

```
Leu Leu Lys Lys Leu Lys Lys Leu Leu Lys Lys Leu
1               5                   10
```

( 2 ) INFORMATION FOR SEQ ID NO:114:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:114:

```
Lys Leu Leu Lys Lys Leu Lys Lys Leu Leu Lys Lys Leu
1               5                   10
```

( 2 ) INFORMATION FOR SEQ ID NO:115:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:115:

```
Lys Lys Leu Leu Lys Lys Leu Lys Lys Leu Leu Lys Lys Leu
1               5                   10
```

( 2 ) INFORMATION FOR SEQ ID NO:116:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:116:

```
Leu Lys Lys Leu Leu Lys Lys Leu Lys Lys Leu Leu Lys Lys Leu
1               5                   10                  15
```

( 2 ) INFORMATION FOR SEQ ID NO:117:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:117:

```
Leu Lys Lys Leu Leu Lys Lys Leu Lys Lys Leu Leu Lys Arg
1               5                   10
```

( 2 ) INFORMATION FOR SEQ ID NO:118:

( i ) SEQUENCE CHARACTERISTICS:
        ( A ) LENGTH: 7 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:118:

Lys Phe Ala Lys Lys Phe Ala
1               5

(2) INFORMATION FOR SEQ ID NO:119:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:119:

Lys Ile Ala Lys Lys Ile Ala
1               5

(2) INFORMATION FOR SEQ ID NO:120:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:120:

Arg Phe Ala Arg Arg Phe Ala
1               5

(2) INFORMATION FOR SEQ ID NO:121:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:121:

Lys Phe Ala Lys Phe Ala Lys Lys Phe Ala
1               5                   10

(2) INFORMATION FOR SEQ ID NO:122:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

Lys Lys Phe Ala Lys Phe Ala Lys Lys Phe Ala
1               5                   10

(2) INFORMATION FOR SEQ ID NO:123:

(i) SEQUENCE CHARACTERISTICS:
        (A) LENGTH: 11 amino acids
        (B) TYPE: amino acid
        (C) STRANDEDNESS: single -continued ( D ) TOPOLOGY: linear ( i i ) MOLECULE TYPE: peptide ( x i ) SEQUENCE DESCRIPTION: SEQ ID NO:123:

Lys  Lys  Leu  Ala  Lys  Leu  Ala  Lys  Lys  Leu  Ala
    1                      5                          10

( 2 ) INFORMATION FOR SEQ ID NO:124:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:124:

Lys  Leu  Ala  Lys  Leu  Ala  Lys  Lys  Leu  Ala
    1                      5                     10

( 2 ) INFORMATION FOR SEQ ID NO:125:

( i ) SEQUENCE CHARACTERISTICS:
            ( A ) LENGTH: 14 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:125:

Lys  Phe  Ala  Lys  Lys  Phe  Ala  Lys  Phe  Ala  Lys  Lys  Phe  Ala
    1                      5                          10

( 2 ) INFORMATION FOR SEQ ID NO:126:

( i ) SEQUENCE CHARACTERISTICS:
            ( A ) LENGTH: 14 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:126:

Arg  Phe  Ala  Arg  Arg  Phe  Ala  Arg  Phe  Ala  Arg  Arg  Phe  Ala
    1                      5                          10

( 2 ) INFORMATION FOR SEQ ID NO:127:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:127:

Glu  Lys  Lys  Leu  Leu  Lys  Lys  Leu  Lys  Lys  Leu
    1                      5                          10

( 2 ) INFORMATION FOR SEQ ID NO:128:

( i ) SEQUENCE CHARACTERISTICS:
            ( A ) LENGTH: 11 amino acids
            ( B ) TYPE: amino acid
            ( C ) STRANDEDNESS: single (D) TOPOLOGY: linear (ii) MOLECULE TYPE: peptide (xi) SEQUENCE DESCRIPTION: SEQ ID NO:128:

```
Lys  Lys  Lys  Leu  Leu  Lys  Lys  Leu  Lys  Lys  Leu
1                 5                      10
```

(2) INFORMATION FOR SEQ ID NO:129:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:129:

```
Lys  Leu  Lys  Lys  Lys  Phe  Leu  Lys  Lys  Leu
1                 5                      10
```

(2) INFORMATION FOR SEQ ID NO:130:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:130:

```
Leu  Lys  Lys  Leu  Leu  Glu  Lys  Leu  Lys  Lys  Leu
1                 5                      10
```

(2) INFORMATION FOR SEQ ID NO:131:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:131:

```
Leu  Lys  Lys  Leu  Leu  Lys  Glu  Leu  Lys  Lys  Leu
1                 5                      10
```

(2) INFORMATION FOR SEQ ID NO:132:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: one-of(1, 2, 5, 8, 9)
        (D) OTHER INFORMATION: /note="Xaa=ornithine."

(xi) SEQUENCE DESCRIPTION: SEQ ID NO:132:

```
Xaa  Xaa  Leu  Leu  Xaa  Glu  Leu  Xaa  Xaa  Leu
1                 5                      10
```

(2) INFORMATION FOR SEQ ID NO:133:

( i ) SEQUENCE CHARACTERISTICS:
 ( A ) LENGTH: 12 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:133:

```
Leu  Lys  Lys  Leu  Leu  Lys  Lys  Leu  Lys  Lys  Leu  Cys
  1              5                      10
```

( 2 ) INFORMATION FOR SEQ ID NO:134:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: one-of(1, 2, 5, 8, 9)
  ( D ) OTHER INFORMATION: /note="Xaa=ornithine."

( x i ) SEQUENCE DESCRIPTION: SEQ ID NO:134:

```
Xaa  Xaa  Leu  Leu  Xaa  Asp  Leu  Xaa  Xaa  Leu
  1              5                      10
```

( 2 ) INFORMATION FOR SEQ ID NO:135:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:135:

```
Lys  Lys  Phe  Gly  Lys  Lys  Phe  Val  Lys  Ile  Leu  Lys  Lys
  1              5                      10
```

( 2 ) INFORMATION FOR SEQ ID NO:136:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:136:

```
Lys  Trp  Lys  Leu  Phe  Lys  Lys  Ile  Glu  Lys  Val
  1              5                      10
```

( 2 ) INFORMATION FOR SEQ ID NO:137:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:137:

```
Leu  Lys  Lys  Leu  Leu  Lys  Lys
1                5
```

( 2 ) INFORMATION FOR SEQ ID NO:138:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:138:

```
Leu  Lys  Lys  Leu  Leu  Lys  Leu  Leu  Lys
1                5
```

( 2 ) INFORMATION FOR SEQ ID NO:139:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:139:

```
Lys  Lys  Leu  Leu  Lys  Lys  Leu  Lys  Lys  Leu  Leu  Lys  Lys  Leu
1                5                          10
```

( 2 ) INFORMATION FOR SEQ ID NO:140:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: one-of(2, 5, 6, 8, 9)
        ( D ) OTHER INFORMATION: /note="Xaa=ornithine."

( x i ) SEQUENCE DESCRIPTION: SEQ ID NO:140:

```
Leu  Xaa  Leu  Leu  Xaa  Xaa  Leu  Xaa  Xaa  Leu
1                5                          10
```

( 2 ) INFORMATION FOR SEQ ID NO:141:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa=ornithine."

( x i ) SEQUENCE DESCRIPTION: SEQ ID NO:141:

```
Leu  Xaa  Lys  Leu  Leu  Lys  Lys  Leu  Lys  Lys  Leu
1                5                          10
```

( 2 ) INFORMATION FOR SEQ ID NO:142:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: one-of(2, 3, 6, 7, 9, 10)
    ( D ) OTHER INFORMATION: /note="Xaa=ornithine."

( x i ) SEQUENCE DESCRIPTION: SEQ ID NO:142:

```
Leu  Xaa  Xaa  Leu  Leu  Xaa  Xaa  Leu  Xaa  Xaa  Leu
 1              5                        10
```

( 2 ) INFORMATION FOR SEQ ID NO:143:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: one-of(1, 2, 5, 6, 8, 9)
    ( D ) OTHER INFORMATION: /note="Xaa=ornithine."

( x i ) SEQUENCE DESCRIPTION: SEQ ID NO:143:

```
Xaa  Xaa  Leu  Leu  Xaa  Xaa  Leu  Xaa  Xaa  Leu
 1              5                        10
```

( 2 ) INFORMATION FOR SEQ ID NO:144:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: one-of(1, 2, 5, 8, 9)
    ( D ) OTHER INFORMATION: /note="Xaa=ornithine."

( x i ) SEQUENCE DESCRIPTION: SEQ ID NO:144:

```
Xaa  Xaa  Leu  Leu  Xaa  Gln  Leu  Xaa  Xaa  Leu
 1              5                        10
```

( 2 ) INFORMATION FOR SEQ ID NO:145:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:145:

```
Arg  Leu  Leu  Arg  Arg  Leu  Arg  Arg  Leu
 1              5
```

( 2 ) INFORMATION FOR SEQ ID NO:146:

( i ) SEQUENCE CHARACTERISTICS:

(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:146:

Val Lys Lys Leu Leu Lys Lys Leu Lys Lys Leu
1               5                   10

(2) INFORMATION FOR SEQ ID NO:147:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:147:

Lys Lys Leu Leu Lys Lys Leu Lys Lys Leu Leu Lys Lys Leu
1               5                   10

(2) INFORMATION FOR SEQ ID NO:148:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:148:

Lys Leu Lys Lys Leu Lys Lys Leu Phe Lys
1               5                   10

(2) INFORMATION FOR SEQ ID NO:149:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:149:

Gly Ile Lys Lys Phe Leu Lys Lys Ala Gly Lys Phe Gly Lys Ala Phe
1               5                   10                  15

(2) INFORMATION FOR SEQ ID NO:150:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:150:

Ile Ala Gly Ala Ile Ala Lys Ile Ala Gly Lys Ile Ala Lys Ile Ala
1               5                   10                  15
Gly Ala Ile Ala
        20

(2) INFORMATION FOR SEQ ID NO:151:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:151:

Leu Lys Lys Leu Leu Lys Glu Leu Leu Lys Leu
1               5                   10

(2) INFORMATION FOR SEQ ID NO:152:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:152:

Lys Val Ala Leu Lys Ala Leu Lys Val Ala Leu Lys Ala Leu Lys
1               5                   10                  15
Val Ala Leu Lys Ala Leu
            20

(2) INFORMATION FOR SEQ ID NO:153:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:153:

Lys Ile Ala Lys Lys Ile Ala Lys Ile Ala Lys Lys Ile Ala
1               5                   10

BIOLOGICALLY ACTIVE PEPTIDES HAVING N-TERMINAL SUBSTITUTIONS

This is a continuation of application Ser. No. 08/184,462, filed Jan. 18, 1994; which is a continuation-in-part of application Ser. No. 07/891,201 filed Jun. 1, 1992, now abandoned.

This invention relates to biologically active peptides. More particularly, this invention relates to biologically active peptides having N-terminal (or amino-terminal) substitutions.

In accordance with an aspect of the present invention, there is provided an N-terminal substituted peptide or protein having the formula:

wherein X is a biologically active peptide or protein. The peptide or protein is preferably an ion channel-forming peptide or protein. T is a lipophilic moiety, and W is T or hydrogen.

The term "lipophilic," as used herein, means that the lipophilic moiety enhances the interaction of the peptide or protein with a lipid membrane, such as, for example, a cell membrane.

Lipophilic moieties which may be employed, include, but are not limited to, any moiety which may be placed on the N-terminal of the peptide through a condensation reaction with nitrogen. The lipophilic moiety T may be, for example, a carboxylic acid, a phosphoric acid, preferably an alkylphosphoric acid, a phosphonic acid, preferably an alkylphosphonic acid, a sulfonic acid, preferably an alkylsulfonic acid, or an alkyl group. Preferably, T is:

wherein R is a hydrocarbon having at least two and no more than 16 carbon atoms.

In one embodiment, R is an alkyl group. The alkyl group may be a straight chain or branched chain alkyl group; or a cycloalkyl group. For example, R may be $CH_3(CH_2)_n$—, wherein n is from 1 to 14. Preferably, n is from 3 to 12, more preferably from 4 to 11, still more preferably from 6 to 11, and most preferably n is 6, whereby T is an octanoyl group.

In another embodiment, R is an aromatic (including phenyl and naphthyl), or an alkyl aromatic group. For example, R may be

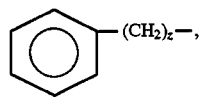

wherein z is from 0 to 6. Preferably, z is 1 or 2.

In another embodiment, R is

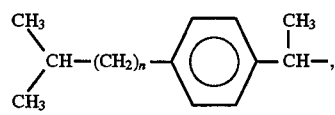

wherein n is from 1 to 5. Preferably n is 1, whereby R is an ibuprofyl group.

In yet another embodiment, T is:

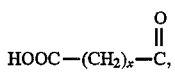

wherein x is from 1 to 14.

Preferably, x is 2, and T is a succinyl group.

In another embodiment, T is:

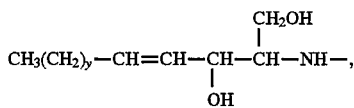

wherein y is from 1 to 14. Preferably, y is 12, whereby T is a sphingosine group.

In yet another embodiment, T is:

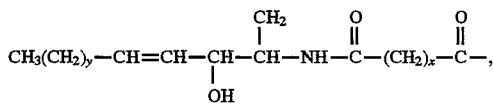

wherein x and y are hereinabove described. Preferably, x is 2, and y is 12.

In one embodiment, W is hydrogen.

Applicant has found, that when biologically active peptides have substitutions at the N-terminal such as those hereinabove described, such peptides have increased biological activity against target cells, viruses, and virally-infected cells, as compared with unsubstituted peptides or peptides substituted at the N-terminal with an acetyl group. Applicant also has found that the N-terminal substitutions hereinabove described significantly increase the biological activity of "short" peptides, i.e. peptides having no more than 14 amino acid residues.

As hereinabove stated, the biologically active peptides or proteins of the present invention are preferably ion channel-forming peptides. An ion channel-forming peptide or protein or ionophore is a peptide or protein which increases the permeability for ions across a natural or synthetic lipid membrane. B. Christensen, et el., PNAS, Vol. 85, pgs. 5072–5076 (July 1988) describes methodology which indicates whether or not a peptide or protein has ion channel-forming properties and is therefore an ionophore. As used herein, an ion channel-forming peptide or ion channel-forming protein is a peptide or protein which has ion channel-forming properties as determined by the method of Christensen, et el.

An amphiphilic peptide or protein is a peptide or protein which includes both hydrophobic and hydrophilic peptide or protein regions.

The ion channel-forming peptides employed in the present invention are generally water soluble to a concentration of at least 20 mg/ml at neutral pH in water. In addition, the structure of such peptide provides for flexibility of the peptide molecule. Such peptides are capable of forming an alpha-helical structure. When the peptide is placed in water, it does not assume an amphiphilic structure. When the peptide encounters an oily surface or membrane, the peptide chain folds upon itself into a rodlike structure.

In general, such peptides have at least 7 amino acids, and in many cases have at least 20 amine acids. In most cases, such peptides do not have in excess of 40 amino acids.

The peptides and/or analogues or derivatives thereof may be administered to a host; for example a human or non-human animal, in an amount effective to inhibit grouch of a target cell, virus, or virally-infected cell. Thus, for example, the peptides and/or analogues or derivatives thereof may be used as antimicrobial agents, anti-viral agents, anti-bacterial agents, anti-tumor agents, anti-parasitic agents, spermicides, as well as exhibiting other bioactive functions.

The term "anti-microbial" as used herein means that the polypeptides or proteins of the present invention inhibit, prevent, or destroy the growth or proliferation of microbes such as bacteria, fungi, viruses, or the like.

The term "anti-bacterial" as used herein means that the peptides or proteins employed in the present invention produce effects adverse to the normal biological functions of bacteria, including death or destruction and prevention of the growth or proliferation of the bacteria when contacted with the peptides or proteins.

The term "antibiotic" as used herein means that the peptides or proteins employed in the present invention produce effects adverse to the normal biological functions of the non-host cell, tissue or organism, including death or destruction and prevention of the growth or proliferation of the non-host cell, tissue, or organism when contacted with the peptides or proteins.

The term "spermicidal" as used herein means that the peptides or proteins employed in the present invention, inhibit, prevent, or destroy the motility of sperm.

The term "anti-fungal" as used herein means that the peptides or proteins employed in the present invention inhibit, prevent, or destroy the growth or proliferation of fungi.

The term "antiviral" as used herein means that the peptides or proteins employed in the present invention inhibit, prevent, or destroy the growth or proliferation of viruses, or of virally-infected cells.

The term "anti-tumor" as used herein means that the peptides or proteins inhibits the growth of or destroys tumors, including cancerous tumors.

The term "anti-parasitic" as used herein means that the peptides or proteins employed in the present invention inhibit, prevent, or destroy the growth or proliferation of parasites.

The peptides or proteins of the present invention have a broad range of potent antibiotic activity against a plurality of microorganisms including gram-positive and gram-negative bacteria, fungi, protozoa, and the like, as well as parasites. The peptides or proteins of the present invention allow a method for treating or controlling microbial infection caused by organisms which are sensitive to the peptides or proteins. Such treatment may comprise administering to a heat organism or tissue susceptible to or affiliated with a microbial infection an antimicrobial amount of at least one of the peptides or proteins.

Because of the antibiotic, antimicrobial, antiviral, and antibacterial properties of the peptides or proteins, they may also be used as preservatives or sterilants or disinfectants of materials susceptible to microbial or viral contamination.

The peptides or proteins and/or derivatives or analogues thereof may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide or protein compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptides or proteins of the present invention may be administered to a host; in particular a human or non-human animal, in an effective antibiotic and/or anti-tumor and/or anti-fungal and/or anti-vital and/or anti-microbial and/or antibacterial and/or anti-parasitic and/or spermicidal amount.

Depending on the use, a composition in accordance with the invention will contain an effective anti-microbial amount and/or an effective spermicidal amount and/or an effective anti-fungal amount and/or an effective anti-viral amount and/or an effective anti-tumor amount and/or an effective anti-parasitic and/or an effective antibiotic amount of one or more of the peptides or proteins of the present invention which have such activity. The peptides or proteins may be administered by direct application of the peptides or proteins to the target cell or virus or virally-infected cell, or indirectly applied through systemic administration.

The peptides or proteins of the present invention may also be employed in promoting or stimulating healing of a wound in a host.

The term "wound healing" as used herein includes various aspects of the wound healing process.

These aspects include, but ere not limited to, increased contraction of the wound, increased deposition of connective tissue, as evidenced by, for example, increased deposition of collagen in the wound, and increased tensile strength Of the wound, i.e., the peptides or proteins increase wound breaking strength. The peptides or proteins of the present invention may also be employed so as to reverse the inhibition of wound healing caused by conditions which depress or compromise the immune system.

The peptides or proteins of the present invention may be used in the treatment of external burns and to treat and/or prevent skin and burn infections. In particular, the peptides or proteins may be used to treat skin and burn infections caused by organisms such as, but not limited to, *P. aeruginosa* and *S. aureus*.

The peptides or proteins are also useful in the prevention or treatment of eye infections. Such infections may be caused by bacteria such as, but not limited to, *P. aeruginosa, S. aureus,* and *N. gonorrhoeae,* by fungi such as but not limited to *C. albicans* and *A. fumigatus,* by parasites such as but not limited to *A. castellani,* or by viruses.

The peptides or proteins may also be effective in killing cysts, spores, or trophozoites of infection—causing organisms. Such organisms include, but are not limited to Acanthamoeba which forms trophozoites or cysts, *C. albicans,* which forms spores, and *A. fumigatus,* which forms spores as well.

The peptides or proteins may also be administered to plants in an effective antimicrobial or antiviral or antiparasitic amount to prevent or treat microbial or viral or parasitic contamination thereof.

The peptides or proteins may also be employed in treating septic shock in that such peptides neutralize bacterial endotoxins. In general, the peptides or proteins are positively charged, while in general, the bacterial endotoxins are negatively charged. The peptides or proteins are particularly useful in that such compounds neutralize bacterial endotoxins without neutralizing essential proteins in plasma (such as heparin, for example).

The peptides or proteins, when used in topical compositions, are generally present in an amount of at least 0.1%, by weight. In most cases, it is not necessary to employ the peptide in an amount greater than 2.0%, by weight.

In employing such compositions systemically (intramuscular, intravenous, intraperitoneal), the active peptide or protein is present in an amount to achieve a serum level of the peptide of at least about 5 ug/ml. In general, the serum level of peptide or protein need not exceed 500 ug/ml. A preferred serum level is about 100 ug/ml. Such serum levels may be achieved by incorporating the peptide or protein in a composition to be administered systemically at a dose of from 1 to about 10 mg/kg. In general, the peptide(s) or protein(s) need not be administered at a dose exceeding 100 mg/kg.

The peptides or proteins may be produced by known techniques and obtained in substantially pure form. For example, the peptides may be synthesized on an automatic peptide synthesizer. *Journal of the American Chemical Society*, Vol. 85, pgs. 2149–54 (1963). It is also possible to produce such peptides or proteins by genetic engineering techniques. The codons encoding specific amino acids are known to those skilled in the art, and therefore DNA encoding the peptides may be constructed by appropriate techniques, and one may clone such DNA into an appropriate expression vehicle (e.g., a plasmid) which is transfected into an appropriate organism for expression of the peptide or protein.

Upon production or synthesis of the peptide or protein, the N-terminal ($NH_2$ or amino terminal) of the peptide is reacted such that the lipophilic moiety is attached to the N-terminal of the peptide. For example, the reaction may be a condensation reaction with an amine. When the lipophilic moiety T is

the N-terminal is reacted with a carboxylic acid of the formula R—COOH, wherein R is a hydrocarbon having at least 2 carbon atoms. The reaction may be carried out in the presence of a coupling agent, such as, for example, DCC, or DIC, and HOBT, or in the presence of an acid chloride. Such a reaction results in the formation of an N-terminal substituted peptide or protein having the structural formula hereinabove described.

In one embodiment, X is a peptide which is a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acid, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids.

Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Pro, Val, Trp, Tyr, norleucine (Nle), norvaline (Nva), and cyclohexylalanine (Cha). The neutral hydrophilic amino acids may be selected from the class consisting of Asn, Gln, Ser, Thr and homoserine (Hse). The basic hydrophilic amino acids may be selected from the class consisting of Lye, Arg, His, Orn, homoarginine (Har), 2, 4-diaminobutyric acid (Dbu), and p-aminophenylalanine.

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In one embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus the biologically active polypeptide may comprise a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic amino acids, one of C or D is a basic hydrophilic amino acid, and the other of C or D is basic or neutral hydrophilic amino acid. The resulting polypeptide chain, therefore, may have one of the following sequences:

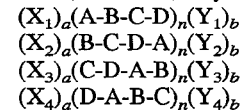

wherein
$X_1$ is D; C-D- or B-C-D-,
$Y_1$ is -A or -A-B or -A-B-C
$X_2$ is A-, D-A- or C-D-A-
$Y_2$ is -B, -B-C or B-C-D
$X_3$ is B-, A-B-, D-A-B-
$Y_3$ is -C, -C-D, -C-D-A
$X_4$ is C-, B-C-, A-B-C-
$Y_4$ is -D, -D-A, -D-A-B
a is 0 or 1; b is 0 or 1
and n is at least 4.

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted groups of four amino acids are not spaced from each other.

As representative examples of such peptides, there may be mentioned.

I Ala-Phe-Ser-Lys-Ala-Phe-Ser-Lys-Ala-Phe-Ser-Lys-Ala-Phe-Ser-Lys-Ala-Phe-Ser-Lys (SEQ ID NO:1)

II Ala-Phe-Ser-Lys-Ala-Phe-Ser-Lys-Ala-Phe-Ser-Lys-Ala-Phe-Ser-Lys-Ala-Phe-Ser-Lys-Ala-Phe-Ser-Lys. (SEQ ID NO:2)

III Phe-Ser-Lys-Ala-Phe-Ser-Lys-Ala-Phe-Ser-Lys-Ala-Phe-Ser-Lys-Ala- (SEQ ID NO:3)

IV Ser-Lys-Ala-Phe-Ser-Lys-Ala-Phe-Ser-Lys-Ala-Phe-Ser-Lys-Ala-Phe-Ser-Lys-Ala-Phe- (SEQ ID NO:4)

V Lys-Ala-Phe-Ser-Lys-Ala-Phe-Ser-Lys-Ala-Phe-Ser-Lys-Ala-Phe-Ser (SEQ ID NO:5)

The peptide may have amino acids extending from either end of the chain. For example, the chains may have a Ser-Lys sequence before the "Ala" end, and/or an Ala-Phe sequence after the "Lys" end. Other amino acid sequences may also be attached to the "Ala" and/or "Lys" end.

Similarly, in any polypeptide chain having at least four groups of amino acids of the sequence as described above, the chain may have, for example, a C-D sequence before the first A-B-C-D group. Also other amino acid sequences may be attached to the "A" and/or the "D" end of one of these polypeptide chains. Also there may be amino acids in the chain which space one or more groups of the hereinabove noted four amino acids from each other.

In accordance with another embodiment, X is magainin peptide.

A magainin peptide is either a magainin such as magainin I, II or III or an analogue or derivative thereof. The magainin peptides preferably include the following basic peptide structure $X_{12}$ —$R_{11}$-$R_{11}$-$R_{12}$-$R_{13}$-$R_{11}$-$R_{14}$-$R_{12}$-$R_{11}$-$R_{14}$-$R_{12}$-$R_{11}$-$R_{11}$-$R_{11}$-$R_{14a}$-$(R_{15})_n$-$R_{14a}$-$R_{14}$— wherein $R_{11}$ is a hydrophobic amino acid, $R_{12}$ is a basic hydrophilic amino acids $R_{13}$ is a hydrophobic, neutral hydrophilic, or basic hydrophilic amino acids $R_{14}$ and $R_{14a}$ are hydrophobic or basic hydrophilic amino acids; $R_{15}$ is glutamic acid or aspartic acid, or a hydrophobic or a basic hydrophilic amino acid, and n is 0 or 1. In a preferred embodiment, $R_{13}$ is a hydrophobic or amino acid, and $R_{15}$ is glutamic acid or aspartic acid.

Thus, for example, a magainin peptide may include the following structure:

-$Y_{12}$-$X_{12}$- where $X_{12}$ is the hereinabove described basic peptide structure and $Y_{12}$ is (i) $R_{12}$ (ii) $R_{14a}$-$R_{12}$ (iii) $R_{11}$-$R_{14a}$-$R_{12}$ (iv) $R_{14}$-$R_{11}$-$R_{14a}$-$R_{12}$ where $R_{11}$, $R_{12}$, $R_{14}$ and $R_{14a}$ are as previously defined.

A magainin peptide may also have the following structure:

-$X_{12}$-$Z_{12}$- wherein $X_{12}$ is as previously defined and $Z_{12}$ is:

(i) $R_{16}$ where $R_{16}$ is a basic hydrophilic amino acid or asparagine or glutamine.

(ii) $R_{16}$-$R_{17}$ where $R_{17}$ is a neutral hydrophilic amino acid, a hydrophobic amino acid, or a basic hydrophilic amino acid. Preferably, $R_{17}$ is a neutral hydrophilic amino acid.

A magainin peptide may also have the following structure:

$(Y_{12})_a$-$X_{12}$-$(Z_{12})_b$ where $X_{12}$, $Y_{12}$ and $Z_{12}$ ere as previously defined and a is 0 or 1 and b is 0 or 1.

The magainin peptides may also include the following basic peptide structure $X_{13}$:

—$R_{14}$-$R_{11}$-$R_{14a}$-$R_{12}$-$R_{11}$-$R_{11}$-$R_{12}$-$R_{13}$- $R_{11}$-$R_{14}$-$R_{12}$-$R_{11}$-$R_{11}$-$R_{12}$-, wherein $R_{11}$, $R_{12}$, $R_{13}$, $R_{14}$, and $R_{14a}$ are amino acids as hereinabove described.

The magainin peptide may also include the following structure $X_{13}$-$Z_{13}$; wherein $X_{13}$ is the hereinabove described basic peptide structure and $Z_{13}$ is $(R_{11})_n$-$(R_{11})_n$-$(R_{11})_n$-$(R_{14a})_n$-$(R_{15})_n$-$(R_{14a})_n$-$(R_{14})_n$-$(R_{16})_n$-$(R_{17})_n$ wherein $R_{11}$, $R_{14}$, $R_{14a}$, $R_{15}$, $R_{16}$, and $R_{17}$ are as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequences as given In the accompanying sequence listing as well as appropriate analogues and derivatives thereof:

(a) (SEQ ID NO:6) (OH) or (NH$_2$) (Magainin I)

(b) (SEQ ID NO:7) (OH) or (NH$_2$) (Magainin II)

(c) (SEQ ID NO:8) (OH) or (NH$_2$) (Magainin III)

The following are examples of peptide derivatives or analogs of the basic structure:

(d) (SEQ ID NO:9) (OH) or (NH$_2$)

(e) (SEQ ID NO:10) (OH) or (NH$_2$)

(f) (SEQ ID NO:11) (OH) or (NH$_2$)

Magainin peptides are described in *Proc. Natl. Acad Sci.* Vol. 84 pp. 5449–53 (Aug. 87). The term "magainin peptides" as used herein refers to the basic magainin structure as well as derivatives and analogs thereof, including but not limited to the representative derivatives or analogs.

In accordance with a further embodiment, X may be a PGLa peptide or an XPF peptide.

A PGLa peptide is either PGLa or an analogue or derivative thereof. The PGLa peptides preferably include the following basic peptide structure $X_{14}$:

-$R_{11}$-$R_{17}$-$R_{12}$-$R_{11}$-$R_{14}$-$R_{14}$-$R_{11}$-$R_{11}$-$R_{14}$-$R_{12}$-$R_{11}$-$R_{11}$-$R_{12}$-$R_{11}$-$R_{11}$-$R_{11}$-$R_{12}$- where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

-$Y_{14}$-$X_{14}$- where $X_{14}$ is as previously defined and $Y_{14}$ is (i) $R_{11}$;

(ii) $R_{14}$-$R_{11}$ where $R_{11}$ and $R_{14}$ are as previously defined.

For example, a PGLa peptide may also have the following structure:

-$X_{14}$-$Z_{14}$- where $X_{14}$ is as previously defined; and $Z_{14}$ is:

(i) $R_{11}$; or (ii) $R_{11}$-$R_{11}$
where $R_{11}$ is as previously defined.
A PGLa peptide may also have the following structure:
$(Y_{14})_a$-$X_{14}$-$(Z_{14})_b$
where $X_{14}$; $Y_{14}$ and $Z_{14}$ are as previously defined, a is 0 or 1 and b is 0 or 1.

An XPF peptide is either XPF or an analogue or derivative thereof. The XPF peptides preferably include the following basic peptide structure $X_{16}$;
—$R_{11}$-$R_{17}$-$R_{12}$-$R_{11}$-$R_{14}$-$R_{18}$-$R_{17}$-$R_{11}$-$R_{14}$-$R_{12}$-$R_{11}$-$R_{11}$-$R_{12}$-$R_{11}$-$R_{11}$-$R_{12}$-$(R_{15})_n$-$R_{11}$—, wherein
$R_{11}$, $R_{12}$, $R_{14}$, $R_{15}$ and $R_{17}$ are as previously defined and $R_{18}$ is glutamine or asparagine or a basic hydrophilic, or hydrophobic amino acid and, n is 0 or 1.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:
-$Y_{16}$-$X_{16}$-
where $X_{16}$ is as previously defined and $Y_{16}$ is
(i) $R_{11}$ or
(ii) $R_{14}$-$R_{11}$
where $R_{11}$ and $R_{14}$ lre as previously defined.
An XPF peptide may include the following structure:
-$X_{16}$-$Z_{16}$-
where $X_{16}$ is as previously defined and $Z_{16}$ is:
(i) $R_{11}$; or
(ii) $R_{11}$-$R_{18}$; or
(iii) $R_{11}$-$R_{18}$-Proline; or (iv) $R_{11}$-$R_{18}$-Proline-$R_{12}$
An XPF peptide may also have the following structure:
$(Y_{16})_a$-$X_{16}$-$(Z_{16})_b$
where $X_{16}$, $Y_{16}$ and $Z_{16}$ are as previously defined: a is 0 or 1 and b is 0 or 1.

Preferred are XPF or PGLa peptides, which are characterized by the following primary amino acid sequences as given in the accompanying sequence listing:
PGLa: (SEQ ID NO:12) (NH$_2$)
XPF: (SEQ ID NO:13)
A review of XPF and PGLa can be found in Hoffman et al, *EMBO J.* 2:711–714, 1983; Andreu, et al, *J. Biochem.* 149:531–535, 1985; Gibson, et al *J. Biol. Chem.* 261:5341–5349, 1986; and Giovannini, et al, *Biochem J.* 243:113–120, 1987.

In accordance with yet another embodiment, X is a CPF peptide or appropriate analogue or derviative thereof.

CPF peptides as well as analogues and derivatives thereof are herein sometimes referred to collectively as CPF peptides.

The CPF peptide may be one which includes the following basic peptide structure $X_{20}$:
$R_{21}$-$R_{21}$-$R_{22}$-$R_{22}$-$R_{21}$-$R_{21}$-$R_{23}$-$R_{21}$-$R_{21}$-$R_{21}$-$R_{23}$-$R_{21}$-$R_{21}$-$R_{24}$-$R_{25}$-$R_{21}$-
wherein $R_{21}$ is a hydrophobic amino acid;
$R_{22}$ is a hydrophobic amino acid or a basic hydrophilic amino acid;
$R_{23}$ is a basic hydrophilic amino acid;
$R_{24}$ is a hydrophobic or neutral hydrophilic amino acid; and
$R_{25}$ is a basic or neutral hydrophilic amino acid.

The hereinabove basic structure is hereinafter symbolically indicated as $X_{20}$.

The hydrophobic amino acids are Ala, Cys, Phe, Gly, Ile, Led, Met, Val, Trp, Tyr, norleucine (Nle), norvaline (Nva), and cyclohexylalanine (Cha).

The neutral hydrophilic amino acids are Asn, Gln, Ser, Thr, and homoserine (Hse).

The basic hydrophilic amino acids are Lys, Arg, His, Orn, homoarginine (Har), 2,4-diaminobutyric acid (Dbu), and p-aminophenylalanine.

The CPF peptide may include only the hereinabove noted amino acids or may include additional amino acids at the amino and/or carboxyl end or both the amino and carboxyl end. In general, the peptide does not include more than 40 amino acids.

The CPF peptides including the above basic structure preferably have from 1 to 4 additional amino acids at the amino end.

Accordingly, such preferred peptides may be represented by the structural formula:
$Y_{20}$-$X_{20}$-
wherein $X_{20}$ is the hereinabove described basic peptide structure and $Y_{20}$ is
(i) $R_{25}$-, or
(ii) $R_{22}$-$R_{25}$-; or
(iii) $R_{21}$-$R_{22}$-$R_{25}$-; or
(iv) $R_{22}$-$R_{21}$-$R_{22}$-$R_{25}$; preferably Glycine-$R_{21}$-$R_{22}$-$R_{25}$.
wherein $R_{21}$, $R_{22}$ and $R_{25}$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:
-$X_{20}$-$Z_{20}$ wherein
X is the hereinabove defined basic peptide structure and $Z_{20}$ is
(i) $R_{21}$-, or
(ii) $R_{21}$-$R_{21}$-; or
(iii) $R_{21}$-$R_{21}$-$R_{24}$; or
(iv) $R_{21}$-$R_{21}$-$R_{24}$-$R_{24}$; or
(v) $R_{21}$-$R_{21}$-$R_{24}$-$R_{24}$-$R_{26}$; or
(vi) $R_{21}$-$R_{21}$-$R_{24}$-$R_{24}$-$R_{26}$-Gln; or
(vii) $R_{21}$-$R_{21}$-$R_{24}$-$R_{24}$-$R_{26}$-Gln-Gln, wherein $R_{21}$ and $R_{24}$ are as previously defined, and $R_{26}$ is proline or a hydrophobic amino acid.

Preferred peptides may be represented by the following structural formula
$(Y_{20})_a$-$X_{20}$-$(Z_{20})_b$
wherein $X_{20}$, $Y_{20}$ and $Z_{20}$ are as previously defined and a is 0 or 1 and b is 0 or 1.

Representative examples of CPF peptides which may be employed, some of which have been described in the literature, include the following sequences as given in the accompanying sequence listing:
(SEQ ID NO:14)
(SEQ ID NO:15)
(SEQ ID NO:16)
(SEQ ID NO:17)
(SEQ ID NO:18)
(SEQ ID NO:19)
(SEQ ID NO:20)
(SEQ ID NO:21)
(SEQ ID NO:22)
(SEQ ID NO:23)
(SEQ ID NO:24)
(SEQ ID NO:25)
(SEQ ID NO:26)
A review of the CPF peptides can be found in Richter, K., Egger, R., and Kreil (1986) J. Biol. Chem 261, 3676–3680; Wakabayashi, T., Kato, H., and Tachibaba, S. (1985) Nucleic Acids Research 13, 1817–1828; Gibson, B. W., Poulter, L., Williams, D. H., and Maggio, J. E. (1986) J. Biol. Chem 261, 5341–5349.

In accordance with yet another embodiment, X is a peptide which includes one of the following basic structures $X_{31}$ through $X_{37}$ wherein:

$X_{31}$ is $-[R_{31}-R_{32}-R_{32}-R_{33}-R_{31}-R_{32}-R_{32}]_{-n}$;
$X_{32}$ is $-[R_{32}-R_{32}-R_{33}-R_{31}-R_{32}-R_{32}-R_{31}]_{-n}$;
$X_{33}$ is $-[R_{32}-R_{33}-R_{31}-R_{32}-R_{32}-R_{31}-R_{32}]_{-n}$;
$X_{34}$ is $-[R_{33}-R_{31}-R_{32}-R_{32}-R_{31}-R_{32}-R_{32}]_{-n}$;
$X_{35}$ is $-[R_{31}-R_{32}-R_{32}-R_{31}-R_{32}-R_{32}-R_{33}]_{-n}$;
$X_{36}$ is $-[R_{32}-R_{32}-R_{31}-R_{32}-R_{32}-R_{33}-R_{31}]_{-n}$; and
$X_{37}$ is $-[R_{32}-R_{31}-R_{32}-R_{32}-R_{33}-R_{31}-R_{32}]_{-n}$;

wherein $R_{31}$ is a basic hydrophilic amino acid, $R_{32}$ is a hydrophobic amino acid, $R_{33}$ is a neutral hydrophilic, basic hydrophilic, or hydrophobic amino acid, and n is from 1 to 5.

The basic hydrophilic amino acids may be selected from the class consisting of Lys, Arg, His, Orn, homoarginine (Har), 2,4-diaminobutyric acid (Dbu), and p-aminophenylalanine.

The hydrophobic amino acids may be selected from the class consisting of Ala, Cys, Phe, Gly, Ile, Leu, Met, Pro, Val, Trp and Tyr,norleucine (Nle), norvaline (Nva), and cyclohexylalanine (Cha).

The neutral hydrophilic amino acids may be selected from the class consisting of Asn, Gln, Set, Thr, and homoserine (Hse).

In accordance with one embodiment, when the peptide includes the structure $X_{31}$, the peptide may include the following structure:

$Y_{31}-X_{31}$, wherein $X_{31}$ is as hereinabove described, and $Y_{31}$ is:
(i) $R_{32}$;
(ii) $R_{32}-R_{32}$;
(iii) $R_{31}-R_{32}-R_{32}$;
(iv) $R_{33}-R_{31}-R_{32}-R_{32}$;
(v) $R_{32}-R_{33}-R_{31}-R_{32}-R_{32}$; or
(vi) $R_{32}-R_{32}-R_{33}-R_{31}-R_{32}-R_{32}$, wherein $R_{31}$, $R_{32}$, and $R_{33}$ are as hereinabove described In accordance with another embodiment, when the peptide includes the structure $X_{31}$, the peptide may include the following structures:

$X_{31}-Z_{31}$, wherein $X_{31}$ is as hereinabove described, and $Z_{31}$ is:
(i) $R_{31}$;
(ii) $R_{31}-R_{32}$;
(iii) $R_{31}-R_{32}-R_{32}$;
(iv) $R_{31}-R_{32}-R_{32}-R_{33}$;
(v) $R_{31}-R_{32}-R_{32}-R_{33}-R_{31}$; or
(vi) $R_{31}-R_{32}-R_{32}-R_{33}-R_{31}-R_{32}$.

In accordance with yet another embodiment, the peptide may include the following structure:

$(Y_{31})_a-X_{31}-(Z_{31})_b$, wherein $Y_{31}$ and $Z_{31}$ are as previously defined, a is 0 or 1, and b is 0 or 1.

When the peptide includes the structure $X_{32}$, the peptide may include the following structure:

$Y_{32}-X_{32}$, wherein $X_{32}$ is as hereinabove described, and $Y_{32}$ is:
(i) $R_{31}$;
(ii) $R_{32}-R_{31}$;
(iii) $R_{32}-R_{32}-R_{31}$;
(iv) $R_{31}-R_{32}-R_{32}-R_{31}$;
(v) $R_{33}-R_{31}-R_{32}-R_{32}-R_{31}$; or
(vi) $R_{32}-R_{33}-R_{31}-R_{32}-R_{32}-R_{31}$.

In another embodiment, when the peptide includes the structure $X_{32}$, the peptide may include the following structure:

$X_{32}-Z_{32}$, wherein $X_{32}$ is as hereinabove described, and $Z_{32}$ is:
(i) $R_{32}$;
(ii) $R_{32}-R_{32}$;
(iii) $R_{32}-R_{32}-R_{33}$;
(iv) $R_{32}-R_{32}-R_{33}-R_{31}$;
(v) $R_{32}-R_{32}-R_{33}-R_{31}-R_{32}$; or
(vi) $R_{32}-R_{32}-R_{33}-R_{31}-R_{32}-R_{32}$.

In accordance with yet another embodiment, the peptide may include the following structure:

$(Y_{32})_1-X_{32}-(Z_{32})_b$, wherein $Y_{32}$ and $Z_{32}$ are as previously defined, a is 0 or 1, and b is 0 or 1.

In accordance with another embodiment, when the peptide includes the structure $X_{33}$, the peptide may include the following structure:

$Y_{33}-X_{33}$ wherein $X_{33}$ is as hereinabove described, and $Y_{33}$ is:
(i) $R_{32}$;
(ii) $R_{31}-R_{32}$;
(iii) $R_{32}-R_{31}-R_{32}$;
(iv) $R_{32}-R_{32}-R_{31}-R_{32}$;
(v) $R_{31}-R_{32}-R_{32}-R_{31}-R_{32}$; or
(vi) $R_{33}-R_{31}-R_{32}-R_{32}-R_{31}-R_{32}$, wherein $R_{31}$, $R_{32}$, and $R_{33}$ are as hereinabove described.

In accordance with another embodiment, when the peptide includes the structure $X_{33}$, the peptide may include the following structure:

$X_{33}-Z_{33}$ wherein $X_{33}$ is as hereinabove described, and $Z_{33}$ is:
(i) $R_{32}$;
(ii) $R_{32}-R_{33}$;
(iii) $R_{32}-R_{33}-R_{31}$;
(iv) $R_{32}-R_{33}-R_{31}-R_{32}$;
(v) $R_{32}-R_{33}-R_{31}-R_{32}-R_{32}$;
(vi) $R_{32}-R_{33}-R_{31}-R_{32}-R_{32}-R_{31}$.

In accordance with yet another embodiment, the peptide may include the following structure:

$(Y_{33})_a-X_{33}-(Z_{33})_b$, wherein $Y_{33}$ and $Z_{33}$ are as previously defined, a is 0 or 1, and b is 0 or 1.

In accordance with yet another embodiment, when the peptide includes the structure $X_{34}$, the peptide may include the following structure:

$Y_{34}-X_{34}$, wherein $X_{34}$ is as hereinabove described, and $Y_{34}$ is:
(i) $R_{32}$;
(ii) $R_{32}-R_{32}$;
(iii) $R_{31}-R_{32}-R_{32}$;
(iv) $R_{32}-R_{31}-R_{32}-R_{32}$;
(v) $R_{32}-R_{32}-R_{31}-R_{32}-R_{32}$; or
(vi) $R_{31}-R_{32}-R_{32}-R_{31}-R_{32}-R_{32}$, wherein $R_{31}$, $R_{32}$ and $R_{33}$ are as hereinabove described.

In accordance with another embodiment, when the peptide includes the structure $X_{34}$, the peptide may include the following structure:

$X_{34}-Z_{34}$, wherein $X_{34}$ as is hereinabove described, and $Z_{34}$ is:
(i) $R_{33}$;
(ii) $R_{33}-R_{31}$;
(iii) $R_{33}-R_{31}-R_{32}$;
(iv) $R_{33}-R_{31}-R_{32}-R_{32}$;
(v) $R_{33}-R_{31}-R_{32}-R_{32}-R_{31}$; or
(vi) $R_{33}-R_{31}-R_{32}-R_{32}-R_{31}-R_{32}$.

In accordance with yet another embodiment, the peptide may include the following structure:

$(Y_{34})_a-X_{34}-(Z_{34})_b$, wherein $X_{34}$ and $Z_{34}$ are as previously defined, a is 0 or 1, and b is 0 or 1.

In accordance with a further embodiment, when the peptide includes the structure $X_{35}$, the peptide may include the following structure:

$Y_{35}-X_{35}$, wherein $X_{35}$ is as hereinabove described, and $Y_{35}$ is:
(i) $R_{33}$;
(ii) $R_{32}-R_{33}$;
(iii) $R_{32}-R_{32}-R_{33}$;
(iv) $R_{31}-R_{32}-R_{32}-R_{33}$;
(v) $R_{32}-R_{31}-R_{32}-R_{32}-R_{33}$; or
(vi) $R_{32}-R_{32}-R_{31}-R_{32}-R_{32}-R_{33}$, wherein $R_{31}$, $R_{32}$, and $R_{33}$ are as hereinabove described.

In accordance with another embodiment, when the peptide includes the structure $X_{35}$, the peptide may include the following structure:

$X_{35}-Z_{35}$ wherein $X_{35}$ is as hereinabove described, and $Z_{35}$ is:
(i) $R_{31}$;
(ii) $R_{31}-R_{32}$;
(iii) $R_{31}-R_{32}-R_{32}$;
(iv) $R_{31}-R_{31}-R_{32}-R_{31}$;
(v) $R_{31}-R_{32}-R_{32}-R_{31}-R_{32}$; or
(vi) $R_{31}-R_{32}-R_{32}-R_{31}-R_{32}-R_{32}$.

In accordance with yet another embodiment, the peptide may include the following structure:

$(Y_{35})_a-X_{35}(Z_{35})_b$, wherein $X_{35}$ and $Z_{35}$ are as previously defined, a is 0 or 1, and b is 0 or 1.

In accordance with a further embodiment, when the peptide includes the structure $X_{36}$, the peptide may include the following structure:

$Y_{36}-X_{36}$ wherein $X_{36}$ is as hereinabove described, and $Y_{36}$ is:
(i) $R_{31}$;
(ii) $R_{33}-R_{31}$;
(iii) $R_{32}-R_{33}-R_{31}$;
(iv) $R_{32}-R_{32}-R_{33}-R_{31}$;
(v) $R_{31}-R_{32}-R_{32}-R_{33}-R_{31}$; or
(vi) $R_{32}-R_{31}-R_{32}-R_{32}-R_{33}-R_{31}$, and $R_{33}$ are as hereinabove described.

In accordance with another embodiment, when the peptide includes the structure $X_{36}$, the peptide may include the following structure:

$X_{36}-Z_{36}$, wherein $X_{36}$ is as hereinabove described, and $Z_{36}$ is:
(i) $R_{32}$;
(ii) $R_{32}-R_{32}$;
(iii) $R_{32}-R_{32}-R_{31}$;
(iv) $R_{32}-R_{32}-R_{31}-R_{32}$;
(v) $R_{32}-R_{32}-R_{31}-R_{32}-R_{32}$; or
(vi) $R_{32}-R_{32}-R_{31}-R_{32}-R_{32}-R_{33}$.

In accordance with yet another embodiment, the peptide may include the following structure:

$(Y_{36})_a-X_{36}(Z_{36})_b$, wherein $Y_{36}$ and $Z_{36}$ are as previously defined, a is 0 or 1, and b is 0 or 1.

In accordance with one embodiment, when the peptide includes the structure $X_{37}$, the peptide may includes the structure $Y_{37}-X_{37}$, wherein $X_{37}$ is as hereinabove described, and $Y_{37}$ is:
(i) $R_{32}$;
(ii) $R_{31}-R_{32}$;
(iii) $R_{33}-R_{31}-R_{32}$;
(iv) $R_{32}-R_{33}-R_{31}-R_{32}$;
(v) $R_{32}-R_{32}-R_{33}-R_{31}-R_{32}$; or
(vi) $R_{31}-R_{32}-R_{32}-R_{33}-R_{31}-R_{32}$, wherein $R_{31}$, $R_{32}$, and $R_{33}$ are as hereinabove described.

In accordance with a further embodiment, when the peptide includes the structure $X_{37}$, the peptide may include the following structure:

$X_{37}-Z_{37}$ wherein $X_{37}$ is as hereinabove described, and $Z_{37}$ is:

(i) $R_{32}$;
(ii) $R_{32}-R_{31}$;
(iii) $R_{32}-R_{31}-R_{32}$;
(iv) $R_{32}-R_{31}-R_{32}-R_{32}$;
(v) $R_{32}-R_{31}-R_{32}-R_{32}-R_{33}$; or
(vi) $R_{32}-R_{31}-R_{32}-R_{32}-R_{33}-R_{31}$.

In accordance with yet another embodiment, the peptide may include the following structure:

$(Y_{37})_a-X_{37}(Z_{37})_b$, wherein $Y_{37}$ and $Z_{37}$ are as previously defined, a is 0 or 1, and b is 0 or 1.

In a preferred embodiment, n is 3, and most preferably the peptide is of one of the following structures as given in the accompanying sequence listing:

(Lys Ile Ala Gly Lys Ile Ala)$_3$ (SEQ ID NO:27).
(Lys Ile Ala Lys Ile Ala Gly)$_3$ (SEQ ID NO:28).
(Lys Ile Ala Gly Lys Ile Gly)$_3$ (SEQ ID NO:29).
(Lys Leu Ala Gly Lys Leu Ala)$_3$ (SEQ ID NO:30).
(Lys Phe Ala Gly Lys Phe Ala)$_3$ (SEQ ID NO:31).
(Lys Ala Leu Set Lys Ala Leu)$_3$ (SEQ ID NO:32).
(Lys Leu Leu Lys Ala Leu Gly)$_3$ (SEQ ID NO:33).
(Lys Ala Ile Gly Lys Ala Ile)$_3$ (SEQ ID NO:34).
(Gly Ile Ala Lys Ile Ala Lye)$_3$ (SEQ ID NO:35).
(Lys Ile Ala Lys Ile Phe Gly)$_3$ (SEQ ID NO:36).
(Gly Ile Ala Arg Ile Ala Lye)$_3$ (SEQ ID NO:37).
(Lys Phe Ala Arg Ile Ala Gly)$_3$ (SEQ ID NO:38).
(Gly Phe Ala Lys Ile Ala Lys)$_3$ (SEQ ID NO:39).
(Lys Ile Ala Gly Orn Ile Ala)$_3$ (SEQ ID NO:40).
(Lys Ile Ala Arg Ile Ala Gly)$_3$ (SEQ ID NO:41).
(Orn Ile Ala Gly Lys Ile Ala)$_3$ (SEQ ID NO:42).
(Gly Ile Ala Arg Ile Phe Lys)$_3$ (SEQ ID NO:43).
(Lys Nle Ala Gly Lys Nle Ala)$_3$ (SEQ ID NO:44).
(Lys Nle Ala Gly Lys Ile Ala)$_3$ (SEQ ID NO:45).
(Lys Ile Ala Gly Lys Nle Ala)$_3$ (SEQ ID NO:46).
(Lys Nva Ala Gly Lys Nva Ala)$_3$ (SEQ ID NO:47).
(Lys Nva Ala Gly Lys Ile Ala)$_3$ (SEQ ID NO:48).
(Lys Leu Leu Ser Lys Leu Gly)$_3$ (SEQ ID NO:49).
(Lys Leu Leu Ser Lys Phe Gly)$_3$ (SEQ ID NO:50).
(Lys Ile Ala Gly Lys Nva Ala)$_3$ (SEQ ID NO:51).
(His Ile Ala Gly His Ile Ala)$_3$ (SEQ ID NO:52).
(Ala Gly Lys Ile Ala Lys Ile)$_3$ (SEQ ID NO:53).
(Ile Ala Lys Ile Ala Gly Lys)$_3$ (SEQ ID NO:54).
(Lys Ile Ala Gly Arg Ile Ala)$_3$ (SEQ ID NO:55).
(Arg Ile Ala Gly Arg Ile Ala)$_3$ (SEQ ID NO:56).
(Lys Val Ala Gly Lys Ile Ala)$_3$ (SEQ ID NO:57).
(Lys Ile Ala Gly Lys Val Ala)$_3$ (SEQ ID NO:58).
(Ala Lys Ile Ala Gly Lys Ile)$_3$ (SEQ ID NO:59).
(Orn Ile Ala Gly Orn Ile Ala)$_3$ (SEQ ID NO:60).
(Lys Phe Ala Gly Lys Ile Ala)$_3$ (SEQ ID NO:61).
(Lys Ile Ala Gly Lys Phe Ala)$_3$ (SEQ ID NO:62).
(Lys Cha Ala Gly Lys Ile Ala)$_3$ (SEQ ID NO:63).
(Lys Nle Ala Lys Ile Ala Gly)$_3$ (SEQ ID NO:64).
(Arg Ile Ala Gly Lys Ile Ala)$_3$ (SEQ ID NO:65).
(Har Ile Ala Gly Har Ile Ala)$_3$ (SEQ ID NO:66).
(Xaa Ile Ala Gly Lys Ile Ala)$_3$ (SEQ ID NO:67).
(Lys Ile Ala Gly Xaa Ile Ala)$_3$ (SEQ ID NO:68).

In ( SEQ ID NO:67) and (SEQ ID NO:68), Xaa is p-aminophenylalanine.

In accordance with another embodiment, X is a peptide which includes the following basic structure $X_{40}$:

$R_{31}-R_{32}-R_{32}-R_{33}-R_{34}-R_{32}-R_{32}-R_{31}-R_{32}-R_{32}-R_{32}-R_{34}-R_{32}-R_{32}$, wherein $R_{31}$, $R_{32}$, and $R_{33}$ are as hereinabove described, and $R_{34}$ is a basic hydrophilic or hydrophobic amino acid.

In accordance with one embodiment, the peptide may include the following structure:

$Y_{40}-X40$, wherein $X_{40}$ is as hereinabove described, and $Y_{40}$ is:

15

(i) $R_{32}$;
(ii) $R_{32}$-$R_{32}$;
(iii) $R_{34}$-$R_{32}$-$R_{32}$;
(iv) $R_{33}$-$R_{34}$-$R_{32}$-$R_{32}$;
(v) $R_{32}$-$R_{33}$-$R_{34}$-$R_{32}$-$R_{32}$;
(vi) $R_{32}$-$R_{32}$-$R_{33}$-$R_{34}$-$R_{32}$-$R_{32}$, or
(vii) $R_{31}$-$R_{32}$-$R_{32}$-$R_{33}$-$R_{34}$-$R_{32}$-$R_{32}$ wherein $R_{31}$, $R_{32}$, $R_{33}$ and $R_{34}$ are as hereinabove described.

In accordance with another embodiment, X is a peptide which includes the following structure:

$X_{40}$-$Z_{40}$, wherein $X_{40}$ is as hereinabove described and $Z_{40}$ is:

(i) $R_{31}$;
(ii) $R_{31}$-$R_{32}$;
(iii) $R_{31}$-$R_{32}$-$R_{32}$;
(iv) $R_{31}$-$R_{32}$-$R_{32}$-$R_{33}$;
(v) $R_{31}$-$R_{32}$-$R_{32}$-$R_{33}$-$R_{34}$;
(vi) $R_{31}$-$R_{32}$-$R_{32}$-$R_{33}$-$R_{34}$-$R_{32}$; or
(vii) $R_{31}$-$R_{32}$-$R_{32}$-$R_{33}$-$R_{34}$-$R_{32}$-$R_{32}$, wherein $R_{31}$, $R_{32}$, R33, and $R_{34}$ are is hereinabove described.

In accordance with yet another embodiment the peptide may include the following structure:

$(Y_{40})_a$-$X_{40}$-$(Z_{40})_b$, wherein $Y_{40}$ and $Z_{40}$ are as previously defined, a is 0 or 1, and b is 0 or 1. In a preferred embodiment, the peptide has the following structural formula as given in the accompanying sequence listing:

(SEQ ID NO: 69)

In another preferred embodiment, the peptide has the following structural formula is given in the accompanying sequence listing:

(SEQ ID NO: 70)

In accordance with a further embodiment, the peptide has one of the one of the following structural formulae as given in the accompanying sequence listing:

(SEQ ID NO: 71)
(SEQ ID NO: 72)
(SEQ ID NO: 73)
(SEQ ID NO: 74)
(SEQ ID NO: 74)
(SEQ ID NO: 75)
(SEQ ID NO: 76)
(SEQ ID NO: 77)
(SEQ ID NO: 78)
(SEQ ID NO: 79)
(SEQ ID NO: 80)
(SEQ ID NO: 81)
(SEQ ID NO: 82)
(SEQ ID NO: 83)
(SEQ ID NO: 84)
(SEQ ID NO: 85)

In accordance with another embodiment, X is a peptide which includes one of the following structural formulae:

(i)—(Lys Ile Ala Lys Lys Ile Ala)-$_n$,
(ii)—(Lys Phe Ala Lys Lys Phe Ala)$_n$-, and
(iii)—(Lys Phe Ala Lys Lys Ile Ala)$_n$-, wherein n is from 1 to 5. Preferably, n is 3, and the peptide has one of the following structural formulae:

(Lys Ile Ala Lys Lys Ile Ala)$_3$
(SEQ ID NO: 86)
(Lys Phe Ala Lys Lys Phe Ala)$_3$
(SEQ ID NO: 87)
(Lys Phe Ala Lys Lys Ile Ala)$_3$
(SEQ ID NO: 88)

In accordance with another embodiment, the X is a peptide which is selected from the group consisting of the following structural formulae as given in the accompanying sequence listing:

16

(SEQ ID NO: 89)
(SEQ ID NO: 90)
(SEQ ID NO: 91)
(SEQ ID NO: 92)

In accordance with yet another embodiment, X is a cecropin or sarcotoxin.

The term cecropins includes the basic structure as well as analogues and derivatives thereof. The cecropins and analogues and derivatives thereof are described in Ann. Rev. Microbiol. 1987, Vol. 41, pages 103–26, in particular page 108, and in Christensen, et al., PNAS vol. 85, pgs. 5072–76, which are hereby incorporated by reference.

The term sarcotoxins includes the basic materials as well as analogues and derivatives thereof. The sarcotoxins and analogues and derivatives thereof are described in Molecular Entomology, pages 369–78, in particular page 375, Alan R. Liss, Inc. (1987), which is hereby incorporated by reference.

In accordance with another embodiment, X is melittin or an analogue or derivative thereof.

Melittin is an amphipathic peptide consisting of 26 amino acid residues, and is isolated from honeybee (*Apis mellifera*) venom. Harmann, et al., *Hoppe-Sevler's Zeitschrift Physiol. Chem.*, Vol. 348, pgs. 37–50 (1987). Melittin has the following structural formula as represented by the three-letter amino acid code:

| Gly | Ile | Gly | Ala | Val | Leu | Lys | Val | Leu |
|-----|-----|-----|-----|-----|-----|-----|-----|-----|
|     |     |     |     | 5   |     |     |     |     |
| Thr | Thr | Gly | Leu | Pro | Ala | Leu | Ile | Ser |
| 10  |     |     |     |     | 15  |     |     |     |
| Trp | Ile | Lys | Arg | Lys | Arg | Gln | Gln |     |
|     | 20  |     |     |     | 25  |     |     |     |

(SEQ ID NO: 93)

In another embodiment, X is a amphiphilic peptide which includes the following basic structure $X_{50}$:

$R_{41}$-$R_{42}$-$R_{42}$-$R_{41}$-$R_{42}$-$R_{42}$-$R_{41}$-$R_{41}$-$R_{42}$-$R_{41}$-$R_{41}$.

$R_{41}$ is a hydrophobic amino acid, and $R_{42}$ is a basic hydrophilic or neutral hydrophilic amino acid.

In one embodiment, the peptide includes the basic structure $Y_{50}$-$X_{50}$ wherein $X_{50}$ is as hereinabove described and $Y_{50}$ is:

(i) $R_{41}$;
(ii) $R_{42}$-$R_{41}$; or
(iii) $R_{42}$-$R_{42}$-$R_{41}$, wherein $R_{41}$ and $R_{42}$ are as hereinabove described.

In one embodiment, $R_{41}$ is leucine. In another embodiment, $R_{42}$ is lysine. Representative examples of peptides in accordance with this aspect of the present invention include those having the following structures:

(SEQ ID NO: 94)
(SEQ ID NO: 95)
(SEQ ID NO: 96)
(SEQ ID NO: 97)

In accordance with another embodiment, X is an amphiphilic peptide which includes the following basic structure $X_{52}$:

$R_{42}$-$R_{41}$-$R_{42}$-$R_{42}$-$R_{41}$-$R_{41}$-$R_{42}$-$R_{42}$-$R_{41}$-$R_{42}$-$R_{42}$, wherein $R_{41}$ is a hydrophobic amino acid and, $R_{42}$ is a basic hydrophilic or neutral hydrophilic amino acid.

In one embodiment $R_{41}$ is leucine. In another embodiment, $R_{42}$ is lysine.

In one embodiment, the peptide includes the basic structure $Y_{52}$-$X_{52}$, wherein $X_{52}$ is as hereinabove described, and $Y_{52}$ is:

(i) $R_{42}$;
(ii) $R_{41}$-$R_{42}$;
(iii) $R_{41}$-$R_{41}$-$R_{42}$;
(iv) $R_{42}$-$R_{41}$-$R_{41}$-$R_{42}$; or
(v) $R_{42}$-$R_{42}$-$R_{41}$-$R_{41}$-$R_{42}$.

In one embodiment, the peptide may have the following structure;

Lys Lys Leu Leu Lys Lys Leu Lys Lys Leu
                     5                  10

Leu Lys Lys Leu Arg Arg
                 15

(SEQ ID NO: 98)

In another embodiment, the peptide includes the basic structure $X_{52}$-$Z_{52}$, wherein $X_{52}$ is as hereinabove described, and $Z_{52}$ is:
(i) $R_{41}$;
(ii) $R_{41}$-$R_{41}$;
(iii) $R_{41}$-$R_{41}$-$R_{42}$;
(iv) $R_{41}$-$R_{41}$-$R_{42}$-$R_{42}$; or
(v) $R_{41}$-$R_{41}$-$R_{42}$-$R_{42}$-$R_{41}$;

In one embodiment, the peptide may have the following structure:

Lys Leu Lys Lys Leu Leu Lys Lys Leu Lys Lys Leu Leu Lys
                     5                       10

Lys Leu                5                  10
 15

(SEQ ID NO: 99)

In another embodiment, the peptide may include the structure:
$(Y_{52})_a$-$X_{52}$-$(Z_{52})_b$, wherein $X_{52}$, $Y_{52}$ and $Z_{52}$ are as hereinabove described, and a is 0 or 1, and b is 0 or 1.

In another embodiment X is a biologically active amphiphilic peptide which includes the following basic structure $X_{54}$:
$R_{41}$-$R_{42}$-$R_{42}$-$R_{41}$-$R_{41}$-$R_{42}$-$R_{42}$-$R_{41}$-$R_{42}$-$R_{42}$-$R_{41}$-$R_{41}$-$R_{42}$-$R_{42}$-$R_{43}$-,
wherein $R_{41}$ and $R_{42}$ are as hereinabove described, and $R_{43}$ is a neutral hydrophilic amino acid.

In one embodiment, the peptide may have the following structure:
(SEQ ID NO: 100)

In another embodiment, the peptide may have the following structure:
(SEQ ID NO: 101)

In another embodiment, X is a biologically active amphiphilic peptide which includes the following basic structure $X_{56}$:
$R_{41}$-$R_{42}$-$R_{41}$-$R_{41}$-$R_{42}$-$R_{42}$-$R_{41}$-$R_{41}$-$R_{42}$-$R_{42}$-$R_{44}$, wherein $R_{41}$ and $R_{42}$ are as hereinabove described, and $R_{44}$ is a neutral hydrophilic amino acid or proline.

In one embodiment, the peptide may include the structure:
$X_{56}$-$Z_{56}$, wherein $X_{56}$ is as hereinabove described, and $Z_{56}$ is:
(i) -$R_{42}$;
(ii) -$R_{42}$-$R_{42}$;
(iii) -$R_{42}$-$R_{42}$-$R_{41}$;
(iv) -$R_{42}$-$R_{42}$-$R_{41}$-$R_{41}$;
(v) -$R_{42}$-$R_{42}$-$R_{41}$-$R_{41}$-$R_{42}$;
(vi) -$R_{42}$-$R_{42}$-$R_{41}$-$R_{41}$-$R_{42}$-$R_{42}$; or
(vii) $R_{42}$-$R_{42}$-$R_{41}$-$R_{41}$-$R_{42}$-$R_{42}$-$R_{41}$.

In a preferred embodiment, the peptide may have one of the following structures:
(SEQ ID NO: 102); or
(SEQ ID NO: 103).

In another embodiment, X is a biologically active amphiphilic peptide which includes the following basic structure $X_{58}$:
$R_{41}$-$R_{41}$-$R_{42}$-$R_{42}$-$R_{41}$-$R_{42}$-$R_{42}$-$R_{41}$-$R_{41}$-$R_{42}$-$R_{42}$-$R_{41}$-$R_{43}$,
wherein $R_{41}$, $R_{42}$, and $R_{43}$ are as hereinabove In one embodiment, the peptide includes the structure $X_{58}$-$Z_{58}$, wherein $X_{58}$ is as hereinabove described, and $Z_{58}$ is:
(i) -$R_{41}$;
(ii) -$R_{41}$-$R_{45}$;
(iii) -$R_{41}$-$R_{45}$-$R_{45}$;
(iv) -$R_{41}$-$R_{45}$-$R_{45}$-$R_{43}$;
(v) -$R_{41}$-$R_{45}$-$R_{45}$-$R_{43}$-$R_{41}$;
(vi) -$R_{41}$-$R_{45}$-$R_{45}$-$R_{43}$-$R_{41}$-$R_{43}$;
(vii) -$R_{41}$-$R_{45}$-$R_{45}$-$R_{43}$-$R_{41}$-$R_{43}$-$R_{43}$;
(viii) -$R_{41}$-$R_{45}$-$R_{45}$-$R_{43}$-$R_{41}$-$R_{43}$-$R_{43}$-$R_{45}$; or
(ix) -$R_{41}$-$R_{45}$-$R_{45}$-$R_{43}$-$R_{41}$-$R_{43}$-$R_{43}$-$R_{45}$-$R_{43}$, wherein $R_{41}$ and $R_{43}$ are as hereinabove described, and $R_{45}$ is proline.

In one embodiment, the peptide has the following structure:
(SEQ ID NO: 104).

In another embodiment, X is a biologically active amphiphilic peptide which includes the following basic structure $X_{60}$:
$R_{41}$-$R_{41}$-$R_{43}$-$R_{42}$-$R_{41}$-$R_{41}$-$R_{41}$-$R_{41}$-$R_{41}$-$R_{41}$-$R_{42}$-$R_{41}$-$R_{41}$-$R_{42}$-$R_{42}$-$R_{41}$-$R_{41}$-$R_{42}$-$R_{42}$-$R_{41}$, wherein $R_{41}$, $R_{42}$, and $R_{43}$ are as hereinabove described in one embodiment, the peptide may have the following structure:
(SEQ ID NO: 105).

In accordance with another embodiment, X is a peptide which includes the following basic structure $X_{62}$:
-$R_{41}$-$R_{42}$-$R_{42}$-$R_{41}$-$R_{42}$-$R_{42}$-$R_{41}$-,
wherein $R_{41}$ and $R_{42}$ are as hereinabove described.

In one embodiment the peptide includes the following structure $Y_{62}$-$X_{62}$, where $X_{62}$ is as hereinabove described, and $Y_{62}$ is:
(i) $R_{41}$;
(ii) $R_{42}$-$R_{41}$;
(iii) $R_{42}$-$R_{42}$-$R_{41}$; or
(iv) $R_{41}$-$R_{42}$-$R_{42}$-$R_{41}$.

Representative examples of such peptides include the following, the sequences of which are given in the accompanying sequence listing:
(SEQ ID NO: 106)
(SEQ ID NO: 107)
(SEQ ID NO: 108)
(SEQ ID NO: 109)
(SEQ ID NO: 110)
(SEQ ID NO: 111)

In one embodiment, the peptide includes the structure $X_{62}$-$Z_{62}$, wherein $X_{62}$ is as hereinabove described, and $Z_{62}$ is:
(i) $R_{41}$
(ii) $R_{41}$-$R_{42}$;
(iii) $R_{41}$-$R_{42}$-$R_{42}$; or
(iv) $R_{41}$-$R_{42}$-$R_{42}$-$R_{41}$, where $R_{41}$ and $R_{42}$ are as hereinabove described.

A representative example includes the following peptide having the structural formula given below and listed in the accompanying sequence listing:
(SEQ ID NO: 112)

In another embodiment, the peptide has the structure $(Y_{62})_1\text{-}X_{62}\text{-}(Z_{62})_b$, wherein $X_{62}$, $Y_{62}$ and $Z_{62}$ are as hereinabove described, a is 0 or 1, and b is 0 or 1.

Representative examples of such peptides include the following, the structures of which are given in the accompanying sequence listing:
(SEQ ID NO: 113)
(SEQ ID NO: 114)
(SEQ ID NO: 115)
(SEQ ID NO: 116)

In another embodiment, X is a peptide having the following structural formula:
(SEQ ID NO: 117)

In another embodiment, X is a biologically active amphiphilic peptide including the following basic structure $X_{64}$:
$R_{42}\text{-}R_{42}\text{-}R_{42}\text{-}R_{41}\text{-}R_{41}\text{-}R_{42}\text{-}R_{42}\text{-}R_{41}\text{-}$,
wherein $R_{41}$ and $R_{42}$ are as hereinabove described.

In one embodiment, the peptide may include the structure $Y_{64}\text{-}X_{64}\text{-}$, wherein $X_{64}$ is as hereinabove described, and $Y_{64}$ is:
(i) $\text{-}R_{41}$; or
(ii) $R_{42}\text{-}R_{41}$.

In another embodiment, the peptide may include the structure $X_{64}\text{-}Z_{64}$, wherein $X_{64}$ is as hereinabove described, and $Z_{64}$ is:
(i) $R_{42}\text{-}$;
(ii) $R_{42}\text{-}R_{42}$; or
(iii) $R_{42}\text{-}R_{42}\text{-}R_{41}$.

In yet another embodiment, the peptide has the structure:
$(Y_{64})_a\text{-}X_{64}\text{-}(Z_{64})_b$, wherein $X_{64}$, $Y_{64}$, and $Z_{64}$ are as hereinabove described, a is 0 or 1, and b is 0 or 1.

Representative examples of such peptides include the following:
(SEQ ID NO: 127)
(SEQ ID NO: 128)
(SEQ ID NO: 129)

In yet another embodiment, X is a biologically active amphiphilic peptide including the following basic structure $X_{66}$:
$R_{41}\text{-}R_{42}\text{-}R_{42}\text{-}R_{41}\text{-}R_{41}\text{-}R_{46}\text{-}R_{42}\text{-}R_{41}\text{-}R_{42}\text{-}R_{42}\text{-}R_{41}$, wherein $R_{41}$ and $R_{42}$ are hereinabove described and $R_{46}$ is glutamic acid. A representative example of such a peptide is the following:
(SEQ ID NO: 130)

In yet another embodiment, X is a biologically active amphiphilic peptide including the following basic structure $X_{68}$:
$\text{-}R_{42}\text{-}R_{42}\text{-}R_{41}\text{-}R_{41}\text{-}R_{42}\text{-}R_{46}\text{-}_{41}\text{-}R_{42}\text{-}R_{42}\text{-}R_{41}\text{-}$, wherein $R_{41}$, $R_{42}$, and $R_{46}$ are hereinabove described.

In one embodiment, the peptide includes the following basic structure $Y_{68}\text{-}X_{68}$, wherein $X_{68}$ is as hereinabove described, and $Y_{68}$ is:
(i) $R_{41}$.

Representative examples of such peptides include the following:
(SEQ ID NO: 131)
(SEQ ID NO: 132).

In another embodiment, X is a biologically active amphiphilic peptide including the following basic structure $X_{70}$:
$\text{-}R_{41}\text{-}R_{42}\text{-}R_{42}\text{-}R_{41}\text{-}R_{41}\text{-}R_{42}\text{-}R_{42}\text{-}R_{41}\text{-}R_{42}\text{-}R_{42}\text{-}R_{41}\text{-}R_{41}\text{-}$, wherein $R_{41}$ and $R_{42}$ are hereinabove described. A representative example of such a peptide has the following structure:
(SEQ ID NO: 133).

In another embodiment, X is a biologically active amphiphilic peptide including the following basic structure $X_{72}$:
$\text{-}R_{42}\text{-}R_{42}\text{-}R_{41}\text{-}R_{41}\text{-}R_{42}\text{-}R_{47}\text{-}R_{41}\text{-}R_{42}\text{-}R_{42}\text{-}R_{41}\text{-}$, wherein $R_{41}$ and $R_{42}$ are hereinabove described, and $R_{47}$ is aspartic acid. A representative example of such a peptide has the following structure:
(SEQ ID NO: 134).

In yet another embodiment, X is a biologically active amphiphilic peptide having the following structure:
(SEQ ID NO: 135).

In yet another embodiment, X is a biologically active amphiphilic peptide including the following structure $X_{74}$:
$R_{42}\text{-}R_{41}\text{-}R_{42}\text{-}R_{41}\text{-}R_{41}\text{-}R_{42}\text{-}R_{42}\text{-}R_{41}\text{-}R_{46}\text{-}R_{42}\text{-}R_{41}$, wherein $R_{41}$, $R_{42}$, and $R_{46}$ are hereinabove described. A representative example of such a peptide has the following structures
(SEQ ID NO: 136).

In another embodiment, X is a biologically active amphiphilic peptide including the following structure $X_{76}$:
$\text{-}R_{41}\text{-}R_{42}\text{-}R_{42}\text{-}R_{41}\text{-}R_{41}\text{-}R_{42}\text{-}$, wherein $R_{41}$ and $R_{42}$ are hereinabove described.

In another embodiment, the peptide includes the structure $Y_{76}\text{-}X_{76}\text{-}$, wherein $X_{76}$ is as hereinabove described, and $Y_{76}$ is:
(i) $\text{-}R_{42}$;
(ii) $\text{-}R_{42}\text{-}R_{42}$;
(iii) $\text{-}R_{41}\text{-}R_{42}\text{-}R_{42}$;
(iv) $\text{-}R_{41}\text{-}R_{41}\text{-}R_{42}\text{-}R_{42}$;
(v) $\text{-}R_{42}\text{-}R_{41}\text{-}R_{41}\text{-}R_{42}\text{-}R_{42}$; or
(vi) $\text{-}R_{42}\text{-}R_{42}\text{-}R_{41}\text{-}R_{41}\text{-}R_{42}\text{-}R_{42}$.

In another embodiment, the peptide includes the structure $\text{-}X_{76}\text{-}Z_{76}$, wherein $X_{76}$ is as hereinabove described, and $Z_{76}$ is:
(i) $R_{48}\text{-}$;
(ii) $R_{48}\text{-}R_{41}\text{-}$; or
(iii) $R_{48}\text{-}R_{41}\text{-}R_{42}\text{-}$, wherein $R_{41}$ and $R_{42}$ are as hereinabove described, and $R_{48}$ is a basic hydrophilic, neutral hydrophilic, or hydrophobic amino acid.

In yet another embodiment, the peptide has the following structural formula:
$(Y_{76})_a\text{-}X_{76}\text{-}(Z_{76})_b$, wherein $X_{76}$, $Y_{76}$, and $Z_{76}$ are as hereinabove described, a is 0 or 1, and b is 0 or 1.

Representative examples of such peptides include the following:
(SEQ ID NO: 137)
(SEQ ID NO: 138)
(SEQ ID NO: 139).

In yet another embodiment, X is a biologically active amphiphilic peptide including the following structural formula $X_{78}$:
$\text{-}R_{41}\text{-}R_{42}\text{-}R_{41}\text{-}R_{41}\text{-}R_{42}\text{-}R_{42}\text{-}R_{41}\text{-}R_{42}\text{-}R_{42}\text{-}R_{41}$, wherein $R_{41}$ and $R_{42}$ are as hereinabove described. A representative example of much a peptide has the following structure:
(SEQ ID NO: 140).

In another embodiment, X has the following structure:
(SEQ ID NO:149).

In another embodiment, X is a biologically active amphiphilic peptide including the following structural formula $X_{80}$:
$\text{-}R_{41}\text{-}R_{42}\text{-}R_{42}\text{-}R_{41}\text{-}R_{41}\text{-}R_{42}\text{-}R_{46}\text{-}R_{41}\text{-}R_{41}\text{-}R_{42}\text{-}R_{41}\text{-}$, wherein $R_{41}$, $R_{42}$, and $R_{46}$ are as hereinabove described. A representative example of such a peptide has the following structure:
(SEQ ID NO: 151).

In accordance with yet another embodiment, X is an ion channel-forming peptide or protein.

Ion channel-forming proteins or peptides which may be employed include defensins, also known as human neutrophil antimicrobial peptides (HNP), major basic protein (MBP) of eosinophils, bactericidal permeability-increasing protein (BPI), and a pore-forming cytotoxin called variously perforin, cytolysin, or pore-forming protein. Defensins are described in Selsted, et el., *J. Clin. Invest.*, Vol. 76, pgs. 1436–1439 (1985). MBP proteins are described in Wasmoen, et al., *J. Biol. Chem.*, Vol. 263, pgs 12559–12563. (1988). BPI proteins are described in Ooi, et el, *J. Biol. Chem.*, Vol. 262, pgs. 14891–14894 (1987). Perforin is described in Hankart, et el., *J. Exp. Med.*, 160: 75 (1984), and in Podack, at el., *J. Exp. Med:*, 160:695 (1984). The above articles are hereby incorporated by reference.

The term ion channel-forming proteins includes the basic structures of the ion channel-forming proteins as well as analogues and derivatives.

In accordance with yet another embodiment, each of the amino acid residues of the peptides or proteins may be a D-amino acid or glycine. Although the scope of this particular embodiment is not to be limited to any theoretical reasoning, it is believed that the above-mentioned peptides or proteins, when consisting entirely of D-amino acid or glycine residues, may have increased resistance to proteolytic enzymes while retaining their activity. Such peptides thus may be administered orally. Also, in accordance with another embodiment, all of the amino acid residues may be D-amino acid or glycine residues, or L-amino acid or glycine residues.

It is also to be understood that the peptides or proteins may be administered in combination with one another.

In accordance with another embodiment, the N-terminal substituted peptides or proteins of the present invention may be employed in combination with an ion having phamacological properties for the purposes hereinabove described.

An ion having pharmacological properties is one which when introduced into a target cell or virus or vitally-infected cell inhibits and/or prevents and/or destroys the growth of the target cell, virus, or vitally-infected cell.

Such an ion having pharmacological properties is one which in the absence of an ion channel forming peptide is unable to cross a natural or synthetic lipid membrane; in particular a cell or virus membrane, in sufficient amounts to affect a cell or virus adversely.

The peptide or protein and ion having pharmacological properties may be administered as a single composition or in separate compositions, and the single or separate compositions may include additional materials, actives and/or inactives, in addition to the peptide or protein and ion having pharmacological properties. As representative examples of ions having pharmacological properties which may be employed, there may be mentioned fluoride, peroxide, bicarbonate, silver, zinc, mercury, arsenic, copper, platinum, antimony, gold, thallium, nickel, selenium, bismuth, and cadmium ions.

The peptide or protein and the ion having pharmacological properties, whether administered or prepared in a single composition or in separate compositions, are employed in amounts effective to inhibit and/or prevent and/or destroy the growth of the target cell, vine, or virally-infected cell. In effect, the ion potentiates the action of the peptide, i.e., the amount of ion As effective to reduce the maximum effective concentration of the peptide or protein for inhibiting growth of a target cell, virus, or virally-infected cell.

The ion having pharmacological properties, when used topically, is generally employed in a concentration of from 0.05% to 2.0%. When used systemically, the ion is generally employed in an amount of from 1 to 10 mg. per kg. of host weight. Peptide or protein dosages may be within the ranges hereinabove described.

It is also to be understood that the peptide or protein and ion having pharmacological properties, may be delivered or administered in different forms; for example, the ion may be administered orally, while the peptide may be administered by IV or IP.

As representative examples of administering the peptide or protein and ion for topical or local administration, the peptide could be administered in an amount of up to about 1% weight to weight and the ion delivered in an amount of about 50 mM (about 0.1%). Alternatively, the ion, in the form of a salt such as sodium fluoride, could be administered orally in conjunction with systemic administration of the peptide or protein. For example, the peptide or protein may be administered IV or IP to achieve a serum dose of 100 micrograms per milliliter (10 milligrams per kilogram) in conjunction with an oral dose of ion, in particular, sodium fluoride, of 10 meq per kilogram.

In accordance with another embodiment, the peptides or proteins of the present invention may be administered to a host in combination with an antibiotic selected from the class consisting of bacitracins, gramacidin, polymyxin, vancomycin, teichoplanin, aminoglycosides, hydrophobic antibiotics, penicillins, monobactams, or derivatives or analogues thereof.

The bacitracins, gramacidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-O-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolids ring known as A-62514 (Abbott); AC-7230 (Toys Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-O-methyl-1-4"-O-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-O-alpha-L-cladinosyl moiety, such as 3-O-alpha-L-cladinosyldeepoxy rosaramicin; tylosins and acyl demycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin, etc.

The peptide or protein and antibiotic may be adminstered by direct administration to a target cell or by systemic or topical administration to a host which includes the target cell, in order to prevent, destroy or inhibit the growth of a target cell. Target cells whose growth may be prevented, inhibited, or destroyed by the administration of the peptides and antibiotic include Gram-positive and Gram-negative bacteria as well as fungal cells.

The antibiotic, such as those hereinabove described, or derivatives or analogues thereof, when used topically, is generally employed in a concetration of about 0.1% to about 10%. When used systemically, the antibiotic or derivative or analogue thereof is generally employed in an amount of from 1.25 mg. to about 45 mg. per kg. of host weight per day. Peptide or protein dosages may be those as hereinabove described.

As representative examples of administering the peptide or protein and antibiotic for topical or local administration, the peptide or protein could be administered in an amount of from about 0.1% to about 10% weight to weight, and the antibiotic is delivered in an amount of from about 0.1% to about 10% weight to weight.

In accordance with another embodiment, the peptides or proteins of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents, may also have anti-fungal activity, and that certain anti-fungal agents may have anti-parasitic activity.

In accordance with another embodiment, the peptides or proteins of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

The present invention will be further described with respect to the following examples; however, the scope of the invention is not to be limited thereby.

EXAMPLE 1

Table I, which follows, indicates the Minimal Inhibitory Concentration (MIC) in µg/ml of various peptides, against *S. aureus* strain ATCC 25923(S), *P. aeruginosa* strain ATCC 27853(P), and *E. coli* ATCC strain 25922(E), and *C. albicans* (CA). A "D" indicates that each amino acid residue is a D-amino acid residue or a glycine residue. The peptides ere unsubstituted at the N-terminal, substituted with an acetyl group at the N-terminal as indicated by Ac-; substituted with an octanoyl group at the N-terminal as indicated by Oct-, substituted with sphingosine as indicated by Sph-; substituted with a succinyl group, as indicated by Suc-; substituted with a hexanoyl group, as indicated by Hex-; substituted with a heptanoyl group, as indicated by Hep; substituted with a valeryl group, as indicated by Val-; substituted with, a myristryl group, as indicated by Myr-; or substituted with an ibuprofyl group, as indicated by Ibu-.

The procedure for the antibacterial assay is based upon the guidelines of the National Committee for Clinical Laboratory Standards, Document M7-T2, Volume 8, No. 8, 1988.

Stock solutions of peptides with and without the appropriate substitutions, are prepared at a concentration of 512 µg/ml in sterile deionized distilled water and stored at $-70°$ C. Each peptide is a C-terminal amide.

The stock peptide solution is diluted in serial dilutions (1:2) down the wells of a microtiter plate so that the final concentrations of peptides in the wells are 0.25, 0.50, 1, 2, 4, 8, 16, 32, 64, 128, and 256 µg/ml. $1-5 \times 10^5$ CFUs/ml of either *S. aureus* ATCC 25923, *E. coli* ATCC 25922, *P. aeruginosa* ATCC 27853, or *C. albicans*, were added to the wells in full strength Mueller Hinton broth (BBL 11443) from a mid-log culture. The inoculum is standardized spectrophotometrically at 600 nm and is verified by colony counts. The plates are incubated for 16–20 hours at 37° C., and the minimal inhibitory concentration (MIC) for each peptide is determined. Minimal inhibitory concentration is defined as the lowest concentration of peptide which produces a clear well in the microtiter plate. The minimal inhibitory concentration of each of the peptides with and/or without the appropriate substitutions is given in Table I below.

TABLE I

| Peptide | Minimal Inhibitory Concentration (µg/ml) | | | |
|---|---|---|---|---|
| | S | P | E | CA |
| Oct-(SEQ ID NO: 27)-NH$_2$ | 2 | 4 | 2 | 16 |
| Oct-(SEQ ID NO: 27)-OH | 8 | 8 | 4 | 32 |
| Ac-(SEQ ID NO: 27)-NH$_2$ | 32 | 128 | 8 | N/A |
| (SEQ ID NO: 27)-NH$_2$ | 8,16 | 64,128 | 8 | N/A |
| (SEQ ID NO: 27)-OH | 128 | 128 | 8 | N/A |
| Sph-Suc-(SEQ ID NO: 27)-NH$_2$ | 64 | >256 | 32 | N/A |
| Suc-(SEQ ID NO: 27)-NH$_2$ | >256 | >256 | 32 | 128 |
| Ibu-(SEQ ID NO: 27)-NH$_2$ | 2 | 4 | 8 | 128 |
| (SEQ ID NO: 66)-NH$_2$ | 4 | 32 | 32 | 64 |
| Oct-(SEQ ID NO: 66)-NH$_2$ | 4 | 16 | 8 | 256 |
| (SEQ ID NO: 86)-OH | 128 | 32 | 2 | 256 |
| Oct-(SEQ ID NO: 86)-OH | 8 | 4 | 2 | 128 |
| Oct-(SEQ ID NO: 106)-NH$_2$ | 128 | 32,64 | 128 | 64,128 |
| Oct-(SEQ ID NO: 107)-NH$_2$ | 128 | 256 | >256 | 128 |
| Oct-(SEQ ID NO: 108)-NH$_2$ | 16 | 4 | 64 | 64 |
| Oct-(SEQ ID NO: 109)-NH$_2$ | 8 | 4 | 16 | 32 |
| (SEQ ID NO: 110)-NH$_2$ | >256 | 32,64 | 64,128 | N/A |
| Ac-(SEQ ID NO: 110)-NH$_2$ | 256 | 8,16 | 32,64 | N/A |
| Oct-(SEQ ID NO: 110)-NH$_2$ | 4 | 4 | 8 | 32 |
| Oct-D-(SEQ ID NO: 110)-NH$_2$ | 4 | 4 | 16 | 32 |
| Hex-(SEQ ID NO: 110)-NH$_2$ | 16 | 8 | 16 | 64 |
| Hep-(SEQ ID NO: 110)-NH$_2$ | 8 | 4 | 16 | 32 |
| Val-(SEQ ID NO: 110)-NH$_2$ | 64 | 8 | 32 | 32 |
| Myr-(SEQ ID NO: 110)-NH$_2$ | 16 | 16 | 16 | >256 |
| Oct-(SEQ ID NO: 111)-NH$_2$ | 64 | 8 | 32 | 32 |
| (SEQ ID NO: 113)-NH$_2$ | 16,32 | 8,16 | 32 | N/A |
| Ac-(SEQ ID NO: 113)-NH$_2$ | 32 | 64 | 64 | N/A |
| Oct-(SEQ ID NO: 113)-NH$_2$ | 8 | 8 | 8 | 128 |

TABLE I-continued

| Peptide | Minimal Inhibitory Concentration (μg/ml) | | | |
|---|---|---|---|---|
| | S | P | E | CA |
| Oct-(SEQ ID NO: 118)-NH$_2$ | >256 | 256 | >256 | >256 |
| Oct-(SEQ ID NO: 119)-NH$_2$ | >256 | >256 | >256 | >256 |
| Oct-(SEQ ID NO: 120)-NH$_2$ | 64 | 128 | 256 | 64 |
| Oct-(SEQ ID NO: 121)-NH$_2$ | 128 | 256 | 256 | 256 |
| Oct-(SEQ ID NO: 122)-NH$_2$ | 32 | 32 | 64 | 64 |
| Oct-(SEQ ID NO: 123)-NH$_2$ | 32 | 16 | 32 | 32 |
| Oct-(SEQ ID NO: 124)-NH$_2$ | 128 | 64 | 256 | 128 |
| Oct-(SEQ ID NO: 125)-NH$_2$ | 8 | 8 | 16 | 64 |
| Oct-(SEQ ID NO: 126)-NH$_2$ | 8 | 8 | 8 | 64 |
| Oct-(SEQ ID NO: 127)-NH$_2$ | >256 | 32 | 32 | 128 |
| Oct-(SEQ ID NO: 128)-NH$_2$ | 128 | 64 | 32 | 32 |
| Oct-(SEQ ID NO: 129)-NH$_2$ | 128 | 16 | 32 | 128 |
| Oct-(SEQ ID NO: 130)-NH$_2$ | 4 | 4 | 4 | 8 |
| Oct-(SEQ ID NO: 131)-NH$_2$ | 8 | 8 | 4 | 64 |
| Oct-(SEQ ID NO: 132)-NH$_2$ | 32 | 8 | 8 | 64 |
| Oct-(SEQ ID NO: 133)-NH$_2$ | 16 | 32 | 32 | 128 |
| Oct-(SEQ ID NO: 134)-NH$_2$ | 64 | 8 | 16 | 64 |
| Oct-(SEQ ID NO: 135)-NH$_2$ | 32 | 8 | 64 | 64 |
| Oct-(SEQ ID NO: 136)-NH$_2$ | 256 | 64 | 256 | 128 |
| Oct-(SEQ ID NO: 137)-NH$_2$ | 256 | 256 | >256 | 256 |
| Oct-(SEQ ID NO: 138)-NH$_2$ | 4 | 8 | 8 | 64 |
| Oct-(SEQ ID NO: 139)-NH$_2$ | 16 | 32 | 16 | 128 |
| Oct-(SEQ ID NO: 140)-NH$_2$ | 32 | 8 | 16 | 64 |
| Oct-(SEQ ID NO: 141)-NH$_2$ | 4 | 4 | 8 | 32 |
| Oct-(SEQ ID NO: 142)-NH$_2$ | 4 | 2 | 8 | 32 |
| Oct-(SEQ ID NO: 143)-NH$_2$ | 16 | 2 | 16 | 16 |
| Oct-(SEQ ID NO: 144)-NH$_2$ | 8 | 4 | 16 | 32 |
| Oct-(SEQ ID NO: 145)-NH$_2$ | 4 | 8 | 16 | 64 |
| Oct-(SEQ ID NO: 146)-NH$_2$ | 8 | 4 | 16 | 32 |
| Oct-(SEQ ID NO: 147)-NH$_2$ | 32 | 32 | 32 | 128 |
| Oct-(SEQ ID NO: 148)-NH$_2$ | 32 | 8 | 32 | 128 |
| (SEQ ID NO: 149)-NH$_2$ | 256 | 32 | 32 | 64 |
| Oct-(SEQ ID NO: 149)-NH$_2$ | 64 | 16 | 32 | 128 |
| Hex-(SEQ ID NO: 150)-NH$_2$ | 16 | 128 | 32 | 128 |
| Myr-(SEQ ID NO: 151)-NH$_2$ | 64 | 128 | 64 | >256 |
| Oct-(SEQ ID NO: 153)-NH$_2$ | 8 | 8 | 32 | 64 |

(2.5 mg/liter) (Sigma Chemical Co., St. Louis, Ill.) plus vitamin K$_1$ (0.25mg/liter) (Sigman Chemical Co., St. Louis, Mo.). For susceptibility testing cultures are taken from overnight (24 hour) broth cultures and diluted in fresh BHI broth (plus hemin plus vitamin K$_1$) to deliver 1×10$^6$ colony-forming units (CFUs)/ml in each microtiter test well.

Antimicrobial susceptibility tests are performed according to the guidelines of the National Committee for Clinical Laboratory Standards (NCCLS) (Document M11-T2, 1989). Microtiter plates (Corning, Corning, N.Y.) are filled aseptically with BHI broth (plus hemin plus vitamin K$_1$) to a volume of 100 μl by the use of a Beckman Biomek 1000 robotic instrument (Beckman Instruments, Palo Alto, Calif.). Peptides are tested in duplicate lanes by adding manually 100 μl of a 1.024 mg/ml peptide solution in water (w/v) to the top wells of a microtiter plate lane. The peptide is diluted serially 1:2 by mixing and transferring 100 μl from the top well down to the bottom well in the lane by use of the Beckman Biomek 1000 (Beckman Instruments, Palo Alto, Calif.). The last 100 μl from the bottom well is discarded. One hundred microliters of the bacteria are added in BHI (plus hemin plus vitamin K$_1$) to each test well to give final peptide dilutions from 0.25 μg/ml. The plates are incubated in the anaerobic chamber at 37° C. for 24–48 hours. After incubation, the minimum inhibitory concentration (MIC) is determined as the lowest concentration of peptide which inhibits growth as determined by visual inspection and optical density when read on a Dynatech MR$_{5000}$ microtiter plate reader at 630 nm (Dynatech Laboratories, Chantilly, Va.). The results are given in Table II below.

TABLE II

| | MIC (μl/ml) | | | | | | |
|---|---|---|---|---|---|---|---|
| | P. gingivalis (strain) | | | | | | |
| Peptide | 381 | A7A1-28 | FAY-19M-1 | 9-14K-1 | W50 | S. mutans | A. viscos |
| (SEQ ID NO: 27)-NH$_2$ | 128 | 16 | 64 | 8,128 | 4 | 16 | 16 |
| Oct-(SEQ ID NO: 27)-NH$_2$ | 16 | 4 | 4 | 4 | 16 | 16 | 16 |
| Oct-(SEQ ID NO: 27)-OH | 2 | 1 | 2 | 2 | 1 | 16 | 32 |
| (SEQ ID NO: 66)-NH$_2$ | 16 | 4 | 8 | 2 | 4 | 8 | 8 |
| Oct-(SEQ ID NO: 66)-NH$_2$ | 4 | 8 | 2 | 2 | 2 | 32 | 16 |
| (SEQ ID NO: 86)-NH$_2$ | 8 | 2 | 8,128 | 8 | 4 | 4 | 16 |
| (SEQ ID NO: 86)-OH | 16 | 4 | 8 | 16 | 4 | 16 | 32 |
| Oct-(SEQ ID NO: 86)-OH | 1 | 1 | 1 | 1 | 1 | 16 | 32 |
| (SEQ ID NO: 152)-NH$_2$ | 32 | 4,8 | 8 | 4 | 4 | 16 | 16 |

The above results indicate that when a biologically active peptide is substituted with a lipophilic moiety of the present invention, the peptide has increased biological activity against a variety of microorganisms.

EXAMPLE 2

Stock cultures of P. gingivalis, S. mutans or A. viscosus are maintained on Brucella blood agar plates with hemin and vitamin K$_1$ (BBL, Cockeysville, Md.) and are grown under anaerobic conditions (Coy Anaerobic Chamber, Ann Arbor, Mich.) with an atmosphere of 80% N$_1$-10%H$_2$-1-%CO$_2$ at 37° C. Experimental cultures are grown up in Brain heart infusion (BHI) broth, (BBL, Cockeysville, Md.) plus hemin

EXAMPLE 3

CD-1 male mice (average body weight, 22.8 g) were inoculated with live E. coli strain 21915-1 (2.3×10$^5$ CFU/mouse) by injection intraperitoneally. Oct-(SEQ ID NO:143)-NH$_2$ then was injected intravenously via the tail vein at 1 and 5 hours post-inoculation. Control mice were inoculated and treated with 0.9% saline. Each different treatment group had 10 mice per group. All control mice died. Treatment doses of Oct-(SEQ ID NO:143)-NH$_2$ were 1, 5, 10, and 20 mg/kg in toto, and resulted in 20%, 40%, 90%, and 90% survival at six days post-inoculation, respectively.

EXAMPLE 4

Oct-(SEQ ID NO:143)-NH$_2$ was injected intravenously into male C57BL/6J mice (average body weight, 20.1 g) approximately two minutes prior to intraperitoneal injection of a solution of lipopolysaccharide (either 0.1 µg or 0.5 µg/mouse) from *E. coli* serotype 0111:B4 and galactosamine (8 mg/mouse). Treatment doses of Oct-(SEQ ID NO:143)-NH$_2$ were 0, 5, 7.5, 10, 12.5, or 15 mg/kg (10 mice/group and when administered prior to 0.5 µg lipopolysaccharide/ mouse resulted in 10%, 0%, 30%, 0%, 50%, and 60% survival at five days post-lipopolysaccharide administration, respectively. When these doses were administered prior to the administration of 0.1 µg lipopolysaccharide/mouse, the results were 40%, 90%, 100%, 100%, 100%, and 100% survival at five days post-lipopolysaccharide administration, respectively.

EXAMPLE 5

A stock solution (10×) of 0.6 mM dye is prepared by adding 1.68 mg of (1-ethyl-2-(3-[1-ethylnaphthol(1,2-d)-thiazolin-2- ylidene]-2-methylpropenyl)naphtho-(1,2-d)-thiazolium bromide (Signa E-7762) to 5 ml of 200 proof ethanol. 1 ml of this solution was added to 9 ml ethanol to give 0.06 mM of dye (60 µM dye).

A stock solution of lipopolysaccharide (LPS) from *E. coli* serotype 0111:B4 was prepared at 1.5 mg/ml. 400 µl of this solution was mixed with 4.6 ml pyrogen free water to give a 120 µg/ml solution.

Row 1 and rows 3 through 12 of a microtiter plate were filled with 100 µl of pyrogen free water or with 10 mg/ml of bovine serum albumin. 200 µl of peptide then is added to row 2 of the microtiter plate at a concentration of 1 ml/ml. 200 µl of pyrogen free water is added to each of the control wells in two lanes (having dye and LPS but no peptide or having dye and no LPS and no peptide). 100 µl then is serially diluted from row 2 through row 12 of the microtiter plate. 50 µl of PBS (pH 7.4) and 50 µl of the LPS solution then are added to row 1 of the plate (blank wells).

Equal volumes of the LPS solution, the dye, and PBS (pH 7.4, approx. 150 mM) are mixed to form a dye-buffer—LPS mixture having LPS at a final concentration of 40 µg/mi and dye at a final concentration of 20 µM. The dye-buffer LPS mixture then is incubated for 10 minutes at room temperature in the dark.

100 µl of the dye-LPS-buffer mixture then is added to every well of the microtiter plate except to the blank wells and to the control lane that does not have LPS or peptide. The plate is incubated for 10 minutes at room temperature in the dark, and the absorbance at 460 nm and 510 nm is read. From these absorbances, the LPS50 value, which is the concentration in mg/ml of peptide necessary to inhibit the binding of 50% of the lipopolysaccharide to the dye, is calculated.

The above procedure was carried out for the peptides listed in Table III below.

TABLE III

| Peptide | LPS50 (µg/ml) |
|---|---|
| Oct-(SEQ ID NO:106)-NH$_2$ | 6.80 |
| Oct-(SEQ ID NO:107)-NH$_2$ | 15.00 |
| Oct-(SEQ ID NO:109)-NH$_2$ | 0.60 |
| Oct-(SEQ ID NO:110)-NH$_2$ | 0.84 |
| Oct-D-(SEQ ID NO:110)-NH$_2$ | 0.97 |

TABLE III-continued

| Peptide | LPS50 (µg/ml) |
|---|---|
| Oct-D-(SEQ ID NO:110)-NH$_2$-melibionic acid | 45.00 |
| Oct-(SEQ ID NO:111)-NH$_2$ | 1.00 |
| Oct-(SEQ ID NO:121)-NH$_2$ | 20.00 |
| Oct-(SEQ ID NO:123)-NH$_2$ | 1.70 |
| Oct-(SEQ ID NO:137)-NH$_2$ | 4.80 |
| Oct-(SEQ ID NO:138)-NH$_2$ | 1.00 |
| Oct-(SEQ ID NO:142)-NH$_2$ | 0.70 |
| Oct-(SEQ ID NO:143)-NH$_2$ | 0.90 |

The peptides or proteins of the present invention, whether administered alone or in combination with agents such as ions having pharmacological properties, antibiotics, or other biologically active peptides or proteins as hereinabove described, may be employed in a wide variety of pharmaceutical compositions in combination with a non-toxic pharmaceutical carrier or vehicle such a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The peptides or proteins and/or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The peptides or proteins may be administered to a host in particular an animal, in an effective antibiotic and/or antitumor and/or antiviral and/or antimicrobial and/or antispermicidal and/or antifungal and/or antiparasitic amount, or in an amount effective to stimulate wound healing in a host, or in an amount effective in treating septic shock in a host. The peptides or proteins may be administered either alone or in combination with an ion having pharmacological properties, antibiotic, or ion channel forming peptide or protein as hereinabove described. When the peptide or protein is administered in combination with an ion having pharmacological properties, the activity of the peptide or protein is potentiated.

When the peptide or protein is administered in combination with an agent as hereinabove described, it is possible to administer the peptide and agent in separate forms. For example, the agent may be administered systemically and the peptide or protein may be administered topically.

When the peptide or protein is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle is preferably free of an oily substance.

The peptide or protein may also be employed alone, or in combination with an ion having pharmacological properties, as hereinabove described in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, gingivitis, and/or to prevent or treat or reduce dental caries. The peptide and ion having pharmacological properties may be used to inhibit, prevent, or destroy the growth of *Streptococcus mutans*, which is associated with dental caries and periodontal disease.

It is to be understood, however, that the scope of the present invention is not to be limited to the specific embodiments described above. The invention may be practiced other than as particularly described and still be within the scope of the accompanying claims.

What is claimed is:

1. A composition for inhibiting growth of a target cell, virus, or virally-infected cell, comprising
(a) an N-terminal substituted peptide having the formula:

wherein X is a biologically active peptide, said peptide being an ion channel-forming peptide, wherein X includes the following basic structure $X_{50}$:
$R_{41}$-$R_{42}$-$R_{41}$-$R_{42}$-$R_{42}$-$R_{41}$-$R_{41}$-$R_{42}$-$R_{41}$-$R_{41}$,
wherein $R_{41}$ is hydrophobic amino acid, and $R_{42}$ is basic hydrophilic or neutral hydrophilic amino acid;
T is a lipophilic moiety, wherein if T is

R is hydrocarbon having at least 2 carbon atoms; and W is T or hydrogen; and
(b) an acceptable pharmaceutical carrier, wherein said peptide is present in an amount effective to inhibit growth of the target cell, virus, or virally-infected cell.

2. The composition of claim 1, wherein X is a biologically active peptide having the following structure:

(SEQ ID NO: 94).

3. The composition of claim 1, wherein X has the structural formula $Y_{50}$-$X_{50}$,
wherein $Y_{50}$ is:
(i) $R_{41}$;
(ii) $R_{42}$-$R_{41}$; or
(iii) $R_{42}$-$R_{42}$-$R_{41}$.

4. The composition of claim 3, wherein X is a biologically active peptide having the following structure:

(SEQ ID NO: 95).

5. The composition of claim 3, wherein X is a biologically active peptide having the following structure:

(SEQ ID NO: 96).

6. The composition of claim 3, wherein X is a biologically active peptide having the following structure:

(SEQ ID NO: 97).

7. A composition for inhibiting growth of a target cell, virus, or virally-infected cell, comprising (a) an N-terminal substituted peptide having the formula:

wherein X is a biologically active peptide, said peptide being an ion channel-forming peptide, wherein X includes the following basic structure $X_{52}$:

$R_{42}$-$R_{41}$-$R_{42}$-$R_{42}$-$R_{41}$-$R_{41}$-$R_{42}$-$R_{42}$-$R_{41}$-$R_{42}$-$R_{42}$, wherein $R_{41}$ is hydrophobic amino acid, and $R_{42}$ is basic hydrophilic or neutral hydrophilic amino acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the; target cell, virus, or virally-infected cell.

8. The composition of claim 7, wherein X has the structural formula $Y_{52}$-$X_{52}$, wherein $Y_{52}$ is:

(i) $R_{42}$;
(ii) $R_{41}$-$R_{42}$;
(iii) $R_{41}$-$R_{41}$-$R_{42}$;
(iv) $R_{42}$-$R_{41}$-$R_{41}$-$R_{42}$; or
(v) $R_{42}$-$R_{42}$-$R_{41}$-$R_{41}$-$R_{42}$.

9. The composition of claim 8, wherein X is a biologically active peptide having the following structure:

(SEQ ID NO: 98).

10. The composition of claim 7, wherein X has the structural formula $X_{52}$-$Z_{52}$, wherein $Z_{52}$ is:

(i) $R_{41}$;
(ii) $R_{41}$-$R_{41}$;
(iii) $R_{41}$-$R_{41}$-$R_{42}$;
(iv) $R_{41}$-$R_{41}$-$R_{42}$-$R_{42}$; or
(v) $R_{41}$-$R_{41}$-$R_{42}$-$R_{42}$-$R_{41}$.

11. The composition of claim 10, wherein X is a biologically active peptide having the following structure:

(SEQ ID NO: 99).

12. A composition for inhibiting growth of a target cell, virus, or virally-infected cell, comprising (a) an N-terminal substituted peptide having the formula:

wherein X is a biologically active peptide, said peptide being an ion channel-forming peptide, wherein X is a peptide that includes the following basic structure $X_{62}$:

-$R_{41}$-$R_{42}$-$R_{42}$-$R_{41}$-$R_{42}$-$R_{42}$-$R_{41}$- wherein $R_{41}$ is hydrophobic amino acid, and $R_{42}$ is basic hydrophilic or neutral hydrophilic amino acid;

T is a lipophilic moiety, wherein if T is

R is hydrocarbon having at least 2 carbon atoms; and, W is T or hydrogen; and (b) an acceptable pharmaceutical carrier, wherein said peptide is present in an amount effective to inhibit growth of the target cell, virus, or virally-infected cell.

13. The composition of claim 12, wherein X is a biologically active peptide having the following structure:

(SEQ ID NO: 106).

14. The composition of claim 12 wherein X includes the structure $Y_{62}$-$X_{62}$, wherein $Y_{62}$ is:

(i) $R_{41}$;
(ii) $R_{42}$-$R_{41}$;
(iii) $R_{42}$-$R_{42}$-$R_{41}$; or
(iv) $R_{41}$-$R_{42}$-$R_{42}$-$R_{41}$.

15. The composition of claim 14 wherein $Y_{62}$ is $R_{42}$-$R_{42}$-$R_{41}$.

16. The composition of claim 14, wherein X is a biologically active peptide having the following structure:

(SEQ ID NO: 107).

17. The composition of claim 14, wherein X is a biologically active peptide having the following structure:

(SEQ ID NO: 108).

18. The composition of claim 14, wherein X is a biologically active peptide having the following structure:

(SEQ ID NO: 109).

19. The composition of claim 14, wherein X is a biologically active peptide having the following structure:

(SEQ ID NO: 110).

20. The composition of claim 14, wherein X is a biologically active peptide having the following structure:

(SEQ ID NO: 111).

21. The composition of claim 14, wherein X is a biologically active peptide having the following structure:

(SEQ ID NO: 141).

22. The composition of claim 14, wherein X is a biologically active peptide having the following structure:

(SEQ ID NO: 142).

23. The composition of claim 14, wherein X is a biologically active peptide having the following structure:

(SEQ ID NO: 143).

24. The composition of claim 23, wherein the lipophilic moiety is an octanoyl moiety.

25. The composition of claim 14, wherein X is a biologically active peptide having the following structure:

(SEQ ID NO: 144).

26. The composition of claim 14, wherein X is a biologically active peptide having the following structure:

(SEQ ID NO: 145).

27. The composition of claim 14, wherein X is a biologically active peptide having the following structure:

(SEQ ID NO: 146).

28. The composition of claim 12, wherein X includes the structure $X_{62}$-$Z_{62}$, wherein $Z_{62}$ is:

(i) $R_{41}$;
(ii) $R_{41}$-$R_{42}$;
(iii) $R_{41}$-$R_{42}$-$R_{42}$; or
(iv) $R_{41}$-$R_{42}$-$R_{42}$-$R_{41}$.

29. The composition of claim 28, wherein X is a biologically active peptide having the following structure:

(SEQ ID NO: 112).

30. The composition of claim 12 wherein X has the structural formula $$(Y_{62})_a\text{-}X_{62}\text{-}(Z_{62})_b,$$

wherein $Y_{62}$ and $Z_{62}$ are the peptide structures of claims 14 and 28, a is 0 or 1, and b is 0 or 1.

31. The composition of claim 30, wherein X is a biologically active peptide having the following structure:
(SEQ ID NO: 113).

32. The composition of claim 30 wherein X is a biologically active peptide having the following structure:
(SEQ ID NO: 114).

33. The composition of claim 30, wherein X is a biologically active peptide having the following structure:
(SEQ ID NO: 115).

34. The composition of claim 30, wherein X is a biologically active peptide having the following structure:
(SEQ ID NO: 116).

35. The composition of claim 30, wherein X is a biologically active peptide having the following structure:
(SEQ ID NO: 117).

36. The composition of claim 30, wherein X is a biologically active peptide having the following structure:
(SEQ ID NO: 147).

37. A composition for inhibiting growth of a target cell, virus, or virally-infected cell, comprising (a) an N-terminal substituted peptide having the formula:

$$\begin{array}{c} W \\ | \\ T-N-X \end{array}$$

wherein X is a biologically active peptide, said peptide being an ion channel-forming peptide, wherein X is a biologically active amphophilic peptide including the following basic structure $X_{64}$:

$$\text{-}R_{42}\text{-}R_{42}\text{-}R_{42}\text{-}R_{41}\text{-}R_{41}\text{-}R_{42}\text{-}R_{42}\text{-}R_{41}\text{-},$$

wherein $R_{41}$ is hydrophobic amino acid, and $R_{42}$ is basic hydrophilic or neutral hydrophilic amino acid;

T is a lipophilic moiety, wherein if T is $$\begin{array}{c} O \\ \| \\ R-C-, \end{array}$$

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

38. The composition of claim 37 wherein X includes the structure $Y_{64}$-$X_{64}$, wherein $Y_{64}$ is:
  (i) -$R_{41}$- or
  (ii) $R_{42}$-$R_{41}$.

39. The composition of claim 37 wherein X includes the structure $X_{64}$-$Z_{64}$, wherein $Z_{64}$ is:
  (i) $R_{42}$-;
  (ii) $R_{42}$-$R_{42}$; or
  (iii) $R_{42}$-$R_{42}$-$R_{41}$.

40. The composition of claim 37 wherein X has the structural formula:

$$(Y_{64})_a\text{-}X_{64}\text{-}(Z_{64})_b,$$

wherein $Y_{64}$ and $Z_{64}$ are the peptide structures defined in claims 28 and 39, a is 0 or 1, and b is 0 or 1.

41. The composition of claim 40 wherein X is a biologically active peptide having the following structure:
(SEQ ID NO: 128).

42. The composition of claim 40, wherein X is a biologically active peptide having the following structure:
(SEQ ID NO: 129).

43. A composition for inhibiting growth of a target cell, virus, or virally-infected cell, comprising (a) an N-terminal substituted peptide having the formula:

$$\begin{array}{c} W \\ | \\ T-N-X \end{array}$$

wherein X is a biologically active peptide, said peptide being an ion channel-forming peptide, wherein X is a biologically active amphophilic peptide including the following basic structure $X_{66}$:

$$\text{-}R_{41}\text{-}R_{42}\text{-}R_{42}\text{-}R_{41}\text{-}R_{41}\text{-}R_{46}\text{-}R_{42}\text{-}R_{41}\text{-}R_{42}\text{-}R_{42}\text{-}R_{41}$$

wherein $R_{41}$ is hydrophobic amino acid, $R_{42}$ is basic hydrophilic or neutral hydrophilic amino acid, and $R_{46}$ is glutamic acid;

T is a lipophilic moiety, wherein if T is $$\begin{array}{c} O \\ \| \\ R-C-, \end{array}$$

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

44. The composition of claim 43, wherein X is a biologically active peptide having the following structure:
(SEQ ID NO: 130).

45. A composition for inhibiting growth of a target cell, virus, or virally-infected cell, comprising (a) an N-terminal substituted peptide having the formula:

$$\begin{array}{c} W \\ | \\ T-N-X \end{array}$$

wherein X is a biologically active peptide, said peptide being an ion channel-forming peptide, wherein X is a biologically active amphophilic peptide including the following basic structure $X_{68}$:

$$\text{-}R_{42}\text{-}R_{42}\text{-}R_{41}\text{-}R_{41}\text{-}R_{42}\text{-}R_{46}\text{-}R_{41}\text{-}R_{42}\text{-}R_{42}\text{-}R_{41},$$

wherein $R_{41}$ is hydrophobic amino acid, $R_{42}$ is basic hydrophilic or neutral hydrophilic amino acid, and $R_{46}$ is glutamic acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

46. The composition of claim 45 wherein X includes the structure $Y_{68}$-$X_{68}$, wherein $Y_{68}$ is:
(i) $R_{41}$.

47. The composition of claim 46, wherein X is a biologically active peptide having the following structure:
(SEQ ID NO: 131).

48. The composition of claim 46, wherein X is a biologically active peptide having the following structure:
(SEQ ID NO: 132).

49. A composition for inhibiting growth of a target cell, virus, or virally-infected cell, comprising (a) an N-terminal substituted peptide having the formula:

wherein X is a biologically active peptide, said peptide being an ion channel-forming peptide, wherein X is a biologically active amphophilic peptide including the following basic structure $X_{70}$:

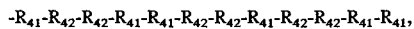

wherein $R_{41}$ is hydrophobic amino acid, $R_{42}$ is basic hydrophilic or neutral hydrophilic amino acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

50. The composition of claim 49, wherein X is a biologically active peptide having the following structure:
(SEQ ID NO: 133).

51. A composition for inhibiting growth of a target cell, virus, or virally-infected cell, comprising (a) an N-terminal substituted peptide having the formula:

wherein X is a biologically active peptide, said peptide being an ion channel-forming peptide, wherein X is a biologically active amphophilic peptide including the following basic structure $X_{72}$:

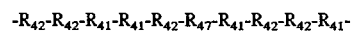

wherein $R_{41}$ is hydrophobic amino acid, $R_{42}$ is basic hydrophilic or neutral hydrophilic amino acid, and $R_{47}$ is aspartic acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

52. The composition of claim 51, wherein X is a biologically active peptide having the following structure:
(SEQ ID NO: 134).

53. A composition for inhibiting growth of a target cell, virus, or virally-infected cell, comprising (a) an N-terminal substituted peptide having the formula:

wherein X is a biologically active peptide, said peptide being an ion channel-forming peptide, wherein X is a biologically active peptide including the following basic structure $X_{76}$:

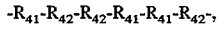

wherein $R_{41}$ is hydrophobic amino acid, and $R_{42}$ is basic hydrophilic or neutral hydrophilic amino acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

54. The composition of claim 53 wherein X includes the structure $Y_{76}$-$X_{76}$ wherein $Y_{76}$ is:
(i) $R_{42}$;
(ii) $R_{42}$-$R_{42}$;
(iii) $R_{41}$-$R_{42}$-$R_{42}$;
(iv) $R_{41}$-$R_{41}$-$R_{42}$-$R_{42}$;
(v) $R_{42}$-$R_{41}$-$R_{41}$-$R_{42}$-$R_{42}$; or
(vi) $R_{42}$-$R_{42}$-$R_{41}$-$R_{41}$-$R_{42}$-$R_{42}$.

55. The composition of claim 53, wherein X includes the structure $X_{76}$-$Z_{76}$, wherein $Z_{76}$ is:
(i) $R_{48}$;
(ii) $R_{48}$-$R_{41}$; or
(iii) $R_{48}$-$R4_{41}$-$R_{42}$;

wherein $R_{41}$ is hydrophobic amino acid, $R_{42}$ is basic hydrophilic or neutral hydrophilic amino acid, and $R_{48}$ is basic hydrophilic, neutral hydrophilic, or hydrophobic amino acid.

56. The composition of claim 53 wherein X has the structural formula: $(Y_{76})_a$-$X_{76}$-$(Z_{76})_b$, wherein $Y_{76}$ and $Z_{76}$ are peptide structures as defined in claims 54 and 55, a is 0 or 1, and b is 0 or 1.

57. The composition of claim 56, wherein X is a biologically active peptide having the following structure:
(SEQ ID NO: 137).

58. The composition of claim 56, wherein X is a biologically active peptide having the following structure:
(SEQ ID NO: 138).

59. The composition of claim 56, wherein X is a biologically active peptide having the following structure:
(SEQ ID NO: 139).

60. A composition for inhibiting growth of a target cell, virus, or virally-infected cell, comprising (a) an N-terminal substituted peptide having the formula:

wherein X is a biologically active peptide, said peptide being an ion channel-forming peptide, wherein X is a biologically active amphiphilic peptide having the following structural formula $X_{78}$:

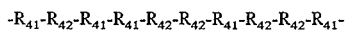
$-R_{41}-R_{42}-R_{41}-R_{41}-R_{42}-R_{42}-R_{41}-R_{42}-R_{42}-R_{41}-$ wherein $R_{41}$ is hydrophobic amino acid, and $R_{42}$ is basic hydrophilic amino acid or neutral hydrophilic amino acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

61. The composition of claim 60, wherein X is a biologically active peptide having the following structure:
(SEQ ID NO: 140).

62. A composition for inhibiting growth of a target cell, virus, or virally-infected cell, comprising (a) an N-terminal substituted peptide having the formula:

wherein X is a biologically active peptide, said peptide being an ion channel-forming peptide, wherein X is a biologically active amphiphilic peptide including the following structural formula $X_{80}$:

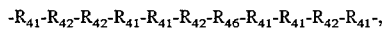
$-R_{41}-R_{42}-R_{42}-R_{41}-R_{41}-R_{42}-R_{46}-R_{41}-R_{41}-R_{42}-R_{41}-,$ wherein $R_{41}$ is hydrophobic amino acid, $R_{42}$ is basic hydrophilic amino acid or neutral hydrophilic amino acid, and $R_{46}$ is glutamic acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the target cell, virus, or virally-infected cell.

63. The composition of claim 62, wherein X is a biologically active peptide having the following structure:
(SEQ ID NO: 151).

64. A composition for inhibiting growth of a target cell, virus, or virally-infected cell, comprising (a) an N-terminal substituted peptide having the formula:

wherein X is a biologically active peptide, said peptide being an ion channel-forming peptide, wherein X includes the following basic structure $X_{54}$:

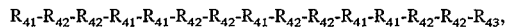
$R_{41}-R_{42}-R_{42}-R_{41}-R_{41}-R_{42}-R_{42}-R_{41}-R_{42}-R_{42}-R_{41}-R_{41}-R_{42}-R_{42}-R_{43},$ wherein $R_{41}$ is hydrophobic amino acid, $R_{43}$ is basic hydrophilic or neutral hydrophilic amino acid, and $R_{43}$ is neutral hydrophilic amino acid;

T is a lipophilic moiety, wherein if T is

R is hydrocarbon having at least 2 carbon atoms; and W is T or hydrogen; and (b) an acceptable pharmaceutical carrier, wherein said peptide is present in an amount effective to inhibit growth of the target cell virus or virally-infected cell.

65. The composition of claim 64, wherein X is a biologically active peptide having the following structure:
(SEQ ID NO: 100).

66. The composition of claim 64, wherein X is a biologically active peptide having the following structure:
(SEQ ID NO: 101).

67. A composition for inhibiting growth of a target cell, virus, or virally-infected cell, comprising (a) an N-terminal substituted peptide having the formula:

wherein X is a biologically active peptide, said peptide being an ion channel-forming peptide, wherein X includes the following basic structure $X_{56}$-$Z_{56}$, wherein $X_{56}$ is:

$R_{41}-R_{42}-R_{41}-R_{41}-R_{42}-R_{42}-R_{41}-R_{41}-R_{42}-R_{42}-R_{44},$ and $Z_{56}$ is:
(i) $R_{42}$;
(ii) $R_{42}$-$R_{42}$;
(iii) $R_{42}$-$R_{42}$-$R_{41}$;
(iv) $R_{42}$-$R_{42}$-$R_{41}$-$R_{41}$;
(v) $R_{42}$-$R_{42}$-$R_{41}$-$R_{41}$-$R_{42}$;
(vi) $R_{42}$-$R_{42}$-$R_{41}$-$R_{41}$-$R_{42}$-$R_{42}$-$R_{41}$, wherein $R_{41}$ is hydrophobic amino acid, $R_{42}$ is basic hydrophilic or neutral hydrophilic amino acid, and $R_{44}$ is neutral hydrophilic amino acid or proline; T is a lipophilic moiety
wherein if T is

R is hydrocarbon having at least 2 carbon atoms; and W is T or hydrogen; and (b) an acceptable pharmaceutical carrier.

wherein said peptide is present in an amount effective to inhibit growth of the target cell, virus, or virally-infected cell.

68. The composition of claim 67 wherein X is a biologically active peptide having the following structure:

(SEQ ID NO: 102).

69. The composition of claim 67, wherein X is a biologically active peptide having the following structure:

(SEQ ID NO: 103).

* * * * *

UNITED STATES PATENT AND TRADEMARK OFFICE
CERTIFICATE OF CORRECTION

PATENT NO. : 5,654,274
DATED : August 5, 1997
INVENTOR(S) : U. Prasad Kari

It is certified that error appears in the above-indentified patent and that said Letters Patent is hereby corrected as shown below:

Claim 7, col. 101, line 24, delete ";" after "the".

Claim 12, col. 102, line 7, delete "," after "and".

Claim 38, col. 103, line 59, "-$R_{41}$- or" should read -- -$R_{41}$-; or --.

Claim 40, col. 104, line 4, "claims 28 and 39" should read --claims 38 and 39--.

Claim 55, col. 106, line 61, "(iii) $R_{48}$-$R4_{41}$-$R_{42}$;" should read --(iii)$R_{48}$-$R_{41}$-$R_{42}$--.

Claim 64, col. 108, line 31, "$R_{43}$" should read --$R_{42}$--.

Signed and Sealed this

Seventh Day of October, 1997

*Attest:*

BRUCE LEHMAN

*Attesting Officer*      *Commissioner of Patents and Trademarks*